United States Patent [19]
Martel et al.

[11] 4,279,835
[45] Jul. 21, 1981

[54] NOVEL CYCLOPROPANE CARBOXYLIC ACID ESTERS

[75] Inventors: Jacques Martel, Bondy; Jean Tessier, Vincennes; Jean-Pierre Demoute, Montreuil-sous-bois, all of France

[73] Assignee: Roussel Uclaf, Paris, France

[21] Appl. No.: 38,728

[22] Filed: May 14, 1979

Related U.S. Application Data

[63] Continuation-in-part of Ser. No. 834,659, Sep. 19, 1977, abandoned, and Ser. No. 5,375, Jan. 22, 1979, abandoned.

[30] Foreign Application Priority Data

Sep. 21, 1976 [FR]  France ............................... 76-28279
Jul. 19, 1977 [FR]  France ............................... 77 22078
Mar. 17, 1978 [FR]  France ............................... 78 07780

[51] Int. Cl.³ ..................... C07C 69/74; A01N 53/00
[52] U.S. Cl. ........................ 260/465 D; 260/326 A; 260/347.4; 260/340.5 R; 560/124; 424/274; 424/282; 424/285; 424/304; 424/305
[58] Field of Search ................... 560/124; 260/465 D; 424/304, 305

[56] References Cited

PUBLICATIONS

Elliott, Nature, vol. 248, No. 5450 p. 710–711, (1974).

Primary Examiner—Natalie Trousof
Assistant Examiner—Michael Shippen
Attorney, Agent, or Firm—Hammond & Littell, Weissenberger and Muserlian

[57] ABSTRACT

Novel cyclopropane carboxylic acid esters of the formula

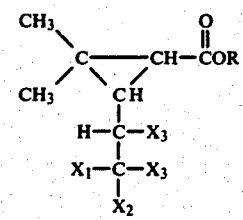

wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is selected from the group consisting of

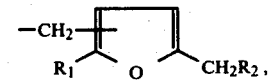

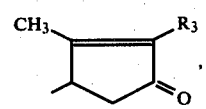

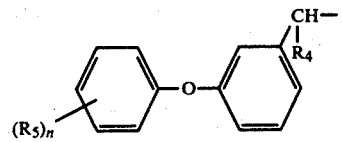

and benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogens, $R_1$ is selected from the group consisting of hydrogen and methyl, $R_2$ is selected from the group consisting of monocyclic aryl and —$CH_2$—C≡CH, $R_3$ is an aliphatic of 2 to 6 carbon atoms having at least one double bond, $R_4$ is selected from the group consisting of hydrogen, —CN and —C≡CH, $R_5$ is selected from the group consisting of chlorine and methyl, n is 0, 1 or 2, $R_6$, $R_7$, $R_8$, and $R_9$ are individually selected from the group consisting of hydrogen, chlorine and methyl and S/I indicates that the ring may be aromatic, dihydro or tetrahydro having pesticidal properties, and a process for their preparation.

16 Claims, No Drawings

NOVEL CYCLOPROPANE CARBOXYLIC ACID ESTERS

PRIOR APPLICATION

This application is a continuation-in-part of our co-pending, commonly assigned U.S. patent application Ser. No. 834,659 filed Sept. 19, 1977, now abandoned and Ser. No. 5,375 filed January 22, 1979 now abandoned.

OBJECTS OF THE INVENTION

It is an object of the invention to provide the novel cyclopropane carboxylic acid esters of formula I and a novel process for their preparation.

It is another object of the invention to provide novel pesticidal compositions containing at least one compound of formula I as the active ingredient.

It is an additional object of the invention to provide a novel process of combatting pests including insects, fungi, acarids, nematodes and ticks.

These and other objects and advantages of the invention will become obvious from the following detailed description.

THE INVENTION

The novel cyclopropane carboxylic acid esters of the invention have the formula

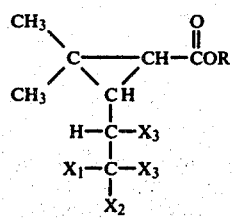

wherein $X_1$ is selected from the group consisting of hydrogen, fluorine, chlorine and bromine, $X_2$ is selected from the group consisting of fluorine, chlorine and bromine, $X_3$ is selected from the group consisting of chlorine, bromine and iodine and R is selected from the group consisting of

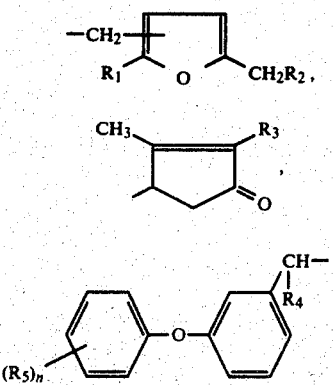

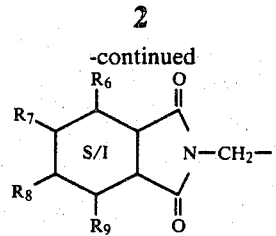

and benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogens, $R_1$ is selected from the group consisting of hydrogen and methyl, $R_2$ is selected from the group consisting of monocyclic aryl and $-CH_2-C \equiv CH$, $R_3$ $_L$ is an aliphatic of 2 to 6 carbon atoms having at least one double bond, $R_4$ is selected from the group consisting of hydrogen, $-CN$ and $-C \equiv CH$, $R_5$ is selected from the group consisting of chlorine and methyl, n is 0, 1 or 2, $R_6$, $R_7$, $R_8$ and $R_9$ are individually selected from the group consisting of hydrogen, chlorine and methyl and S/I indicates that the ring may be aromatic, dihydro or tetrahydro.

Among the preferred groups of formula I, $R_2$ is 5-benzyl-3-furyl-methyl, $R_3$ is vinyl, propen-1-yl, buta-1,3-dienyl or buten-1-yl, $R_5$ is 3-phenoxy-benzyl, α-cyano-3-phenoxy-benzoyl or α-ethynyl-3-phenoxy-benzyl. By convention, in the alcohol moiety of the ester of formula I when n is 0, the ring which is fixed the $R_5$ substituent is then a benzene ring.

The esters of formula I exist in numerous isomeric forms since the cyclopropane carboxylic acids used to form the esters of formula I generally have 3 asymetric carbon atoms, namely the 1- and 3-carbon atoms of the cyclopropane ring and the 1'-carbon atom of polyhalogenated ethyl fixed in the 3-position of the cyclopropane ring. When the three $X_1$, $X_2$ and $X_3$ substituents are all different from each other, an additional asymetric carbon atom exists in the 2'-position of the 3-polyhalogenated ethyl group. Moreover, the alcohol moiety of the esters of formula I may also contain one or more asymetric carbon atoms and/or one or more double bonds making E or Z isomers. The esters of formula I include within their scope any combination of the isomeric form of the compounds existing as racemic mixtures or optical isomer due to the existence of asymetric carbon atoms in the acid moiety and in the alcohol moiety.

In the case when $X_1$ and $X_2$ are identical, to determine the steric configuration of the asymetric carbon atoms in the 1- and 3-position of the cyclopropane ring as well as to determine the structure of the alcohol moiety (which can contain one or more asymetric carbon atoms and/or one or more double bonds), the two diasteroisomeric forms of the esters of formula I or the corresponding free acids due to the existence of the asymetric carbon atoms in the 1'-position can exist and are effectively characterized by their RMN Spectrum or by their rate of migration in thin-layer chromatography and the two diasteroisomers are indicated as the A and B isomers.

Among the preferred carboxylic acids K of the invention for the formation of the esters of formula I are 2,2-dimethyl-3-(1',2'-dichloro-2',2'-dibromoethyl)-cyclopropane-1-carboxylic acids, 2,2-dimethyl-3-(1',2',2',2'-tetrachloroethyl)-cyclopropane-1-carboxylic acids, 2,2-dimethyl-3-(1',2'-dichloro-2',2'-difluoroethyl)-cyclopropane-1-carboxylic acids, 2,2-dimethyl-3-(1',2'-dibromo-2',2'-dichloroethyl)-cyclopropane-1-carboxylic acids, 2,2-dimethyl-3-(1',2'-dibromo-2',2'-difluoroethyl)-cyclopropane-1-carboxylic acids, 2,2-dimethyl-3-(1',2',2',2'-tetrabromoethyl)-cyclopropane-1-carboxylic acids, 2,2-dimethyl-3-(1',2'-diiodo-2',2'-difluoroethyl)-cyclopropane-1-carboxylic acids, 2,2-dimethyl-3-(1',2'-diiodo-2',2'-dichloroethyl)-cyclopropane-1-carboxylic acids, 2,2-dimethyl-3-(1',2'-diiodo-2',2'-dibromoethyl)-cyclopropane-1-carboxylic acids, 2,2-dimethyl-3-(1',2',2'-tribromoethyl)-cyclopropane-1-carboxylic acids, 2,2-dimethyl-3-(1',2'-dichloro-2'-bromoethyl)-cyclopropane-1-carboxylic acids, 2,2-dimethyl-3-(1',2',2'-trichloroethyl)-cyclopropane-1-carboxylic acids, 2,2-dimethyl-3-(1',2'-dibromo-2'-chloroethyl)-cyclopropane-1-carboxylic acids, 2,2-dimethyl-3-(1',2'-dichloro-2'-fuoroethyl)-cyclopropane-1-carboxylic acids, 2,2-dimethyl-3-(1',2'-dibromo-2'-fluoroethyl)-cyclopropane-1-carboxylic acids, 2,2-dimethyl-3-(1',2'-diiodo-2'-fluoroethyl)-cyclopropane-1-carboxylic acids, 2,2-dimethyl-3-(1',2'-diiodo-2'-chloroethyl)-cyclopropane-1-carboxylic acids, 2,2-dimethyl-3-(1',2'-diiodo-2'-bromoethyl)-cyclopropane-1-carboxylic acids, 2,2-dimethyl-3-(1',2',2'-trichloro-2'-fluoroethyl)-cyclopropane-1-carboxylic acids, 2,2dimethyl-3-(1',2'-dibromo-2'-chloro-2'-fluoroethyl)-cyclopropane-1-carboxylic acids, 2,2-dimethyl-3-(1',2',2'-trichloro-2'-bromoethyl)-cyclopropane-1-carboxylic acids, 2,2-dimethyl-3-(1',2',2'-tribromo-2'-chloroethyl)-cyclopropane-1-carboxylic acids, 2,2-dimethyl-3-(1',2',2'-tribromo-2'-fluoroethyl)-cyclopropane-1-carboxylic acids, 2,2-dimethyl-3-(1',2'-dichloro-2'-bromo-2'-fluoroethyl)-cyclopropane-1-carboxylic acids, 2,2-dimethyl-3-(1',2'-diiodo-2'-chloro-2'-fluoroethyl)-cyclopropane-1-carboxylic acids, 2,2-dimethyl-3-(1',2'-diiodo-2'-bromo-2'-fluoroethyl)-cyclopropane-1-carboxylic acids and 2,2-dimethyl-3-(1',2'-diiodo-2'-bromo-2'-chloroethyl)-cyclopropane-1-carboxylic acids.

It is to be understood that the esters of formula I may be prepared from cyclopropane carboxylic acids of (1S, cis) or (1S, trans) structure as well as dl cis [equimolar mixture of (1R, cis) and (1S, cis)] or dl trans [equimolar mixture of (1R, trans) and (1S, trans)] or mixtures of acids of dl-cis and dl-trans structure. The esters of the invention are preferably formed from cyclopropane carboxylic acids of (1R, cis) or (1R, trans) structure as well as acids of dl-cis or dl-trans structure.

Examples of suitable alcohols used to form the esters of formula I are benzyl alcohol, 2,5-dimethyl-4-allylbenzyl alcohol, 5-benzyl-3-furyl-methanol, 5-(propyn-2'-yl)-2-methyl-3-furyl-methanol (kikuthrol), 5-(propyn-2'-yl)-2-furyl-methanol-(prothrol), 1-oxo-2-allyl-3-methyl-cyclopent-2-ene-4-ol (allethrolone), 1-oxo-2-(2',4'-pentadienyl)-3-methylcyclopent-2-ene-4-ol, 1-oxo-2-(2'-butenyl)-3-methyl-cyclopent-2-ene-4-ol, 3-phenoxy-benzyl alcohol, α-cyano-3-phenoxybenzyl alcohol, α-ethynyl-3-phenoxy-benzyl alcohol and 3,4,5,6-tetrahydro-phthalimidomethyl alcohol and especially the optically active form of the alcohols possessing an asymetric carbon atom.

Among the preferred compounds of formula I are those wherein $X_1$ and $X_2$ are identical and are selected from the group consisting of fluorine, bromine or chlorine; those wherein $X_2$ is different from $X_1$; those wherein R is derived from 5-benzyl-3-furyl-methanol, 1-oxo-2-allyl-3-methyl-cyclopent-2-en-4-yl alcohol, 3-phenoxy-benzyl alcohol or α-cyano-3-phenoxy-benzyl alcohol with the alcohol being racemic mixtures or optically active isomers; and those wherein $X_1$ and $X_2$ are identical and are selected from the group consisting of bromine, chlorine and fluorine and R is derived from 5-benzyl-3-furyl-methanol, 1-oxo-2-allyl-3-methyl-cyclopent-2-en-4-yl alcohol, 3-phenoxy-benzyl alcohol or α-cyano-3-phenoxy-benzyl alcohol with the alcohol being in racemic or optically active form.

Particularly preferred compounds of formula I either in the form of their A isomer or B isomer due to the existence of a 1'-asymetrical carbon atom or mixtures of said isomers are (S) α-cyano-3-phenoxy-benzyl 2,2-dimethyl-3S-(1',2',2',2'-tetrabromoethyl)-cyclopropane-1R-carboxylate and (S) α-cyano-3-phenoxy-benzyl 2,2-dimethyl-3S-(1',2'-dibromo-2',2'-dichloroethyl)-cyclopropane-1R-carboxylate as well as the other esters produced in the following examples either in the form of their A or B isomer and mixtures thereof.

The invention is also intended to include the esters of formula I in the form of mixtures of the stereoisomers of cis and trans structure in any proportions. Among these particularly preferred are mixtures of cis and trans structure in weight proportions of 20/80, 50/50 and 80/20.

The novel process of the invention for the preparation of the esters of formula I comprises reacting an ester of the formula

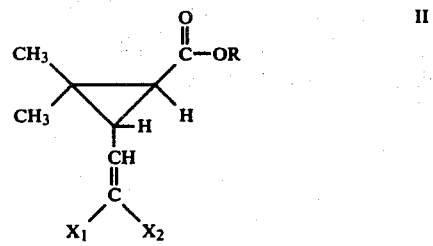

II wherein R, $X_1$ and $X_2$ have the above definition which may be in isomer form with a chlorination, bromination or iodoration agent capable of adding the said halogen across the double bond of the side chain of the cyclopropane carboxylic acid and this process is indicated as process α.

The halogenation agent is preferably chlorine, bromine or iodine and the reaction is preferably effected in an organic solvent not effected by the halogenating agent such as, acetic acid, methylene chloride, carbon tetrachloride or chloroform.

A process of the invention for the preparation of compounds of formula I comprises reacting an acid of the formula

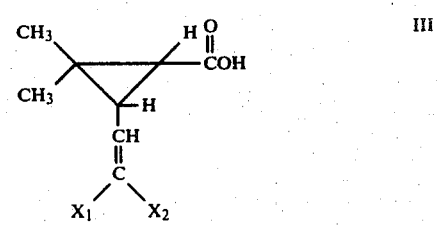

III wherein $X_1$ and $X_2$ have the above definition which may be in isomer form with a chlorination, bromination or iodination agent to form a compound of the formula

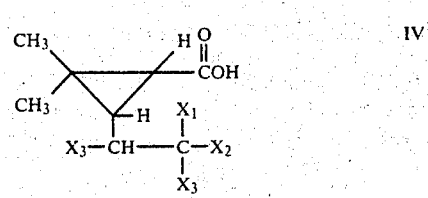

and reacting the said acid or functional derivative thereof with an alcohol of the formula R—OH or a functional derivative thereof wherein R has the above definition and this process is designated as process β.

The halogenation step is effected as in process α and the acid of formula IV is preferably converted to a functional derivative such as the acid chloride, acid anhydride, mixed acid anhydride, lower alkyl ester, metal salt or organic base salt thereof and the alcohol may be used in the form of its bromide, chloride or sulfonate.

In a variation of the β process which will be designated as process γ, a functional derivative of the carboxylic acid of formula III is reacted with a brominating, chlorinating or iodinating agent to form the corresponding functional derivative of the acid of formula IV which is then reacted with the alcohol ROH to form the corresponding ester of formula I.

The halogenation step is effected as in process α and the esterification is effected as in process β. The functional derivative of the acid of formula III may be the acid chloride, acid anhydride or mixed acid anhydride. When the functional derivative of the acid of formula IV is reacted with the alcohol, the reaction is preferably effected in the presence of a basic catalyst. When a metal salt of the acid of formula IV such as an alkali metal, silver or triethylamine salt is used, the alcohol is used in the form of a functional derivative such as its chloride, bromide or sulfonate. Other classical esterification processes may be used to form the esters of formula I.

In processes β and γ, the functional derivative is preferably the acid chloride of formula IV and the esterification of the alcohol ROH is preferably effected in the presence of a tertiary base such as pyridine or triethylamine.

In general, the acids of formula III and the esters of formula II and the functional derivatives of the acids of formula III used as the starting materials are described in the literature such as French Pat. No. 2,185,612 and No. 2,240,914 or can be prepared by processes analogous to those described therein. When $X_1$ and $X_2$ are different halogens, the said esters, acids and their functional derivatives are described in the thesis of Brown (Denton, Texas) of December 1974 entitled "Structure-Activity Studies of Halopyrethroids" or by methods analogous thereto.

It is understood that the esters of formula II and the acids of formula III and their functional derivatives used as starting materials exist in numerous isomeric forms due to the asymmetric carbon atoms in the cyclopropane ring and in the case of esters of formula II due to the possible presence of one or more asymetric carbon atoms and/or one or more double bonds leading to E-Z isomers in the alcohol moiety.

The novel pesticidal compositions of the invention are comprised of a pesticidally effective amount of at least one compound of formula I and an inert carrier. The compositions may also have one or more pesticidal agents and may be in the usual form of powders, granules, suspensions, emulsions, solutions, aerosol solutions, combustible strips or baits or any other classical form. The compositions preferably contains 0.005 to 10% by weight of the active material.

The compositions may contain, in general, a vehicle and/or a non-ionic surface active agent to ensure a uniform dispersion of substances of the mixture. The vehicle may be a liquid such as water, alcohol, hydrocarbons or other organic solvents or a mineral, animal or vegetable oil; a powder such as talc, clays, silicates or kieselguhr; or a combustible solid such as tabu powder or pyrethrum residue.

The compositions possess a remarkable insecticidal activity, particularly an extremely intense lethal activity and a very good stability to atmospheric agents such as heat, light and humidity. The compositions are particularly useful against insects in the agricultural field and are for example, effective against aphis, larvae of Lepidoptera and Coleoptera.

The compositions when used in agriculture are preferably used at a rate of 1 to 100 g of active material per hectare and due to their rapid action, the compositions are also useful as insecticides for household use. Tests have shown the compositions to be useful against houseflies and Spodoptera Littoralis as well as against larvae of Epilachna Varivestris, against Sitophilus Granarius, Tribolium Castaneum and Blatella Germanica. Preferably, the compounds of formula I are in the form of their A or B isomers due to the existence of the asymetric carbon atom in the 1'-position or in the form of mixtures of the said isomers.

To increase the insecticidal activity, the compositions preferably contain a classic synergist for pyrethrum type compounds such as 1-(2,5,8-trioxa-dodecyl-2-propyl-4,5-methylenedioxy)-benzene [piperonyl butoxide], N-(2-ethyl heptyl)-bicyclo [2,2-1]-5-heptene-2,3-dicarboximide or piperonyl-bis-2-(2'-n-butoxyethoxy)-ethyl acetal [tropital] in a weight ratio of 1 to 20 parts of synergist per part of active material. The preferred synergist is piperonyl butoxide.

The pesticidal compositions are also useful for combatting nematodes and acarids and tests have shown the compositions to be effective against Tetranychus Urticae and Ditylenchus Myceliophagus.

The compositions for nematocidal and acaricidal use may be in the form of powders, granules, suspensions, emulsions or solutions and may contain other pesticidal agents. For acaricidal use, the preferred compositions are wettable powders for foliar spraying containing 1 to 80% by weight of the active ingredient or liquids for foliar spraying containing 1 to 500 g/liter of active ingredient or powders for foliar powdering containing 0.05 to 3% by weight of the active ingredient. For nematocidal use, the compositions preferably are sols containing 300 to 500 g/liter of active ingredient. The usual dosage for both uses is 1 to 100 g of active material per hectare.

For acaricidal and nematocidal use, the preferred compounds of formula I are the A and B isomers of (S)α-cyano -3-phenoxy-benzyl 2,2-dimethyl-3S-(1',2',2',2'-tetrabromoethyl)-cyclopropane-1R-carboxylate and the A and B isomers of (S)α-cyano-3-phenoxybenzyl 2,2-dimethyl-3S-(1',2'-dibromo-2',2'-dichloroethyl)-cyclopropane-1R-carboxylate.

The anti-acarien activity of the compositions of the invention permit their use in the form of pharmaceutical compositions for veterinary use to combat parasitic acariens in animals and particularly to combat ixodides and parasitic sarcoptides in animals. Tests have shown the compositions containing at least one compound of formula I to be effective against Rhipicephalus Sanguineus in dogs.

The compositions of the invention are also useful in animals to combat various types of mange such as sarcoptic mange, psoroptic mange and chorioptic mange and are also useful to combat various types of ticks such as ticks of the Boophilus species, the Hyalomnia species, Amblyoma species and the Rhipicephalus species.

The anti-acarienal compositions are useful in veterinary medicine to combat infections due to acariens and may contain more than one active compound of formula I. The compositions may be administered externally as well as orally, rectally or parenterally. The compositions may also contain a synergist for pyrethrum type compounds. The compositions may also be in the form of an addition to animal feed. For example, the animal feed may contain 0.002 to 0.4% by weight of (S) α-cyano-3-phenoxy-benzyl 2,2-dimethyl-3S-(1′,2′,2′,2′-tetrabromoethyl)-cyclopropane-1R-carboxylate.

The novel antifungal compositions of the invention are comprised of an antifungally effective amount of at least one compound of the formula

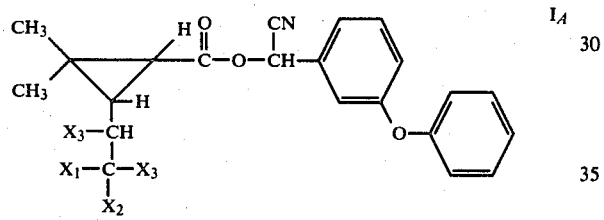

wherein $X_1$, $X_2$ and $X_3$ have the above definition and an inert carrier. The compositions may contain other pesticidal agent and are in the form of powders, granules, suspensions, emulsions, solutions, aerosol solutions or other known types of preparations. The compositions preferably are in the form of sprayable powders containing 25 to 95% by weight of active material or sprayable powders or liquids in a soil containing 10 to 30% by weight of the active material.

The compositions may contain besides the active ingredient, a vehicle and/or a non-ionic, surface-active agent to ensure a uniform dispersion of the ingredients of the mixture. The vehicle may be a liquid such as water, alcohol, hydrocarbons or other organic solvents or a mineral, vegetable or animal oil or a powder such as talc, silicates, clays or kieselguhr.

The antifungal compositions are useful in the agricultural field to combat pathogenic fungi in the vegetation. Tests have shown the compositions to be useful against Fusarium Roseum, Botrytis Cinerea, Phoma Specus and Penicillium Roqueforti. The preferred active ingredients are mixtures of the A and B isomers of (S) α-cyano-3-phenoxy-benzyl 2,2-dimethyl-3S-(1′(RS),2,2′,2′-tetrabromoethyl)-cyclopropane-1R-carboxylate and mixtures of the A and B isomers of (S)α-cyano -3-phenoxy-benzyl 2,2-dimethyl-3S-(1′(RS),2′-dibromo-2′,2′-dichloroethyl)-cyclopropane-1R-carboxylate.

The invention permits the obtaining of novel acids of formula IV and their functional derivatives, especially the acid chlorides in their various isomer forms. The said acids are useful intermediates in the process of the invention to obtain the compounds of formula I.

In the following examples there are described several preferred embodiments to illustrate the invention. However, it is to be understood that the invention is not intended to be limited to the specific embodiments.

EXAMPLE 1

A and B isomer of (S) α-cyano-3-phenoxy-benzyl 2,2-dimethyl -3S-(1′,2′,2′,2′-tetrabromoethyl)-cyclopropane-1R-carboxylate A solution of 2.4 g of bromine in 15 ml of carbon tetrachloride was added to a solution of 7.57 g of (S) α-cyano -3-phenoxy-benzyl 2,2-dimethyl-3R-(2′,2′-dibromovinyl)-cyclo-propane-1R-carboxylate in 100 ml of carbon tetrachloride and the mixture was stirred for 45 minutes at 20° C. and was evaporated to dryness under reduced pressure. The 10 g of residue was chromatographed over silica gel and elution with a 1—1 benzene-petroleum ether (b.p.-35°–75° C.) mixture yielded 4.12 g of isomer A of (S) α-cyano-3-phenoxy-benzyl 2,2-dimethyl -3S-(1′,2′,2′,2′-tetrabromoethyl)-cyclopropane-1R-carboxylate followed by 4 g of isomer B of the said ester. Isomers A and B had a specific rotation of $[α]_D^{20} = -53°$ (c=0.5% in benzene and $+111°$ (c=0.6% in benzene), respectively.

Characteristics of Isomer A

Analysis: $C_{22}H_{19}Br_4NO_3$; molecular weight=665.037 Calculated: %C 39.73; %H 2.88; %Br 48.06; %N 2.11; Found: %C 39.9; %H 2.9; %Br 48.2; %N 2.1.

IR Spectra (chloroform):

absorptions at 1740 cm$^{-1}$ (ester); at 1615, 1588, 1573 and 1488 cm$^{-1}$ (aromatic ring).

RMN Spectrum peaks at 1.25–1.33 ppm (hydrogen of 2-methyl of cyclopropane at 1.75 to 2.17 ppm (hydrogen at 1- and 3-positions of cyclopropane); at 5.19–5.55 ppm (hydrogen at 1′-position of lateral chain); at 6.38 ppm (benzylic hydrogen); and at 6.91 to 7.59 ppm (hydrogens of aromatic ring).

Circular Dichrosim (dioxane)

$Δ^ε = -3$ at 224 nm
$Δ^ε = -4.5$ at 237 nm
$Δ^ε = -0.05$ at 290 nm
more mobile in thin layer chromatography

Characteristics of Isomer B

Analysis: $C_{22}H_{19}Br_4NO_3$; molecular weight=665.037 Calculated: %C 39.73; %H 2.88; %Br 48.06; %N 2.11; Found: %C 39.8; %H 3.0; %Br 48.1; %N 2.0

IR Spectrum (chloroform)

absorption at 1743 cm$^{-1}$ (ester) and at 1615, 1588, 1573 and 1488 cm$^{-1}$ (aromatic ring).

RMN Spectrum peaks at 1.24–1.40 ppm (hydrogens of 2-methyl of cyclopropane) at 1.83 to 2.25 ppm (hydrogens at 1 and 2 of cyclopropane); at 3.98–5.20 ppm (hydrogen in 1′- position of side chain); at 6.39 ppm (benzylic hydrogen); and at 6.92 to 7.52 ppm (hydrogens of aromatic ring).

Circular Dichroism (dioxane)

$\Delta^\epsilon = +4.7$ at 223 nm
$\Delta^\epsilon = +4.2$ at 247 nm
less mobile in thin-layer chromatography

EXAMPLE 2

A and B isomers of (S) α-cyano-3-phenoxy-benzyl 2,2-dimethyl -3S-(2',2'-dichloro-1',2'-dibromo-ethyl)-cyclopropane-1R-carboxylate A solution of 6.55 g of bromine in 20 ml of carbon tetrachloride was added over about 10 minutes to a solution of 17.06 g of (S) α-cyano-3-phenoxy-benzyl 2,2-dimethyl-3R- (2',2'-dichlorovinyl)-cyclopropane-1R-carboxylate in 200 ml of carbon tetrachloride and the mixture was stirred for 48 hours at 20° C. and was evaporated to dryness under reduced pressure. The 23.8 g of raw residue was chromatographed over silica gel and elution with a 7-3 benzene-cyclohexane mixture yielded 10.4 g of isomer A (more mobile in thin-layer chromotography) of (S) α-cyano-3-phenoxy-benzyl 2,2-dimethyl-3S-(2',2'-dichloro-1',2'-dibromoethyl)-cyclopropane-1R-carboxylate and 10 g of isomer B of the same ester (less mobile in thin layer chromatography). Isomer A and B had a specific rotation of $[\alpha]_D = -61°$ (c=0.5% benzene) and +119° (c=1.0% in benzene) respectively.

Characteristics of isomer A

Analysis: $C_{22}H_{19}Br_2Cl_2NO_3$; molecular weight=576.125 Calculated: %C: 45.85; %H: 3.3; %Br: 27.74; %Cl: 12.3; %N: 2.4; Found: %C: 45.8; %H: 3.3; %Br: 27.7; %Cl 12.3; %N 2.3.

IR Spectrum (chloroform)

Absorption at $1738^{-1}$ (ester) and at 1485, 1585 and $1610^{-1}$ (aromatic ring)

RMN Spectrum peaks at 1.29-1.37 ppm (hydrogens of geminal methyls of cyclopropane); at about 2.05 ppm (hydrogens of 1- and 3-positions of cyclopropane); at 5.20-5.29-5.37-5.45 ppm (hydrogens fixed on asymetric carbon of side chain); at 6.45 ppm (benzylic hydrogen); and at 7.0 to 7.6 ppm (hydrogens of aromatic ring)

Circular dichroism (dioxane)

$\Delta^\epsilon = -8$ at 221 nm (inflex.)
$\Delta^\epsilon = +0.14$ at 289 nm (max.)

Characteristics of B isomer

Analysis: $C_{22}H_{19}Br_2Cl_2NO_3$; molecular weight=576.125 Calculated: %C: 45.86; %H: 3.3; %Br: 27.7; %Cl: 12.3; %N: 2.4; Found: %C: 46.2; %H: 3.4; %Br: 27.6; %Cl: 12.2; %N: 2.30.

IR Spectrum absorption at 1740 cm$^{-1}$ (ester) and at 1610, 1585 and 1485 cm$^{-1}$ (aromatic ring)

RMN Spectrum peaks at 1.25-1.38 ppm (hydrogens of geminal methyls of cyclopropane); at 1.87 to 2.3 ppm (hydrogens of 2- and 3-positions of cyclopropane); at 4.97-5.01-5.11-5.16 ppm (hydrogen fixed to asymetric carbon of side chain); at 6.46 ppm (benzyl hydrogen) and at 7 to 7.67 ppm (hydrogens of aromatic ring).

Circular dichroism (dioxane)

$\Delta^\epsilon = +9$ at 220-221 nm (max.)
$\Delta^\epsilon = +0.23$ at 289 nm (max.)

EXAMPLE 3

2,2-dimethyl-3S-(1',2',2',2'-tetrabromoethyl)-cyclopropane-1R-carboxylique acide chloride.

STEP A:

2,2-dimethyl-3S-(1',2',2',2'-tetrabromomethyl)-cyclopropane-1R-carboxylic acid

A solution of 10.4 g of bromine in 22 ml of carbon tetrachloride was added to a mixture of 19.4 g of 2,2-dimethyl -3S-(2',2'-dibromovinyl)-cyclopropane-1R-carboxylic acid in 150 ml of carbon tetrachloride and the mixture was stirred at 20° C. for one hour and was evaporated to dryness under reduced pressure. The 31.4 g of raw product with a melting point of 145° C. was crystallized from 110 ml of carbon tetrachloride to obtain 22.12 g of 2,2-dimethyl-3S-(1',2',2',2'-tetrabromo-ethyl)-cyclopropane-1R-carboxylic acid melting at 150° C.

The product was determined by RMN spectrum to be mixture of A and B isomers which was revealed by one compound (corresponding to about ⅔ of the mixture) presenting peaks at 1.31-1.43 ppm corresponding to hydrogens of geminal methyl groups and at 5.33 to 5.66 ppm corresponding to hydrogen fixed on an asymetrical monobrominated carbon and a second compound (about ⅓ of the mixture) presenting peaks at 1.28-1.48 ppm corresponding to hydrogens of geminal methyl groups and at 4.24 to 5.34 ppm corresponding to hydogen fixed on an asymetrical monobrominated carbon. In the mixture, there were also peaks at 1.67 to 2.17 ppm (hydrogens at 1- and 3-positions of cyclopropane) and towards 11.25 ppm (mobile hydrogen of carboxylic group).

Analysis: $C_8H_{10}Br_4O_2$; molecular weight=457.804 Calculated: %C: 20.99; %H: 2.20; %Br: 69.82; Found: %C: 20.9; %H: 2.2; %Br: 70.2.

STEP B:

2,2-dimethyl-3S-(1',2',2',2'-tetrabromoethyl)-cyclo-propane-1R-carboxylic acid chloride 8.5 ml of thionyl chloride were added to a mixture of 179 ml of petroleum ether (b.p. 35°-75° C.) and 0.2 ml of dimethylformamide and after heating the mixture to reflux, a mixture of 35.76 g of the product of Step A in 150 ml of methylene chloride was added thereto. The mixture was stirred at reflux for 2 hours and was then cooled and evaporated to dryness. The residue was taken up in toluene and the solution was evaporated to dryness under reduced pressure to obtain 38 g of raw 2,2-dimethyl-3S-(1',2',2',2'-tetrabromoethyl)-cyclopropane-1R-carboxylic acid chloride melting at 88° C. which was used as is for the next step.

EXAMPLE 4

(R,S)α-cyano-3-phenoxy-benzyl 2,2-dimethyl-3R-(1',2',2',2',-tetrabromoethyl)-cyclopropane-1R-carboxylate Using the procedure of Example 1, (R,S) α-cyano-3-phenoxy-benzyl 2,2-dimethyl-3S-(2',2'-dibromovinyl)-cyclopropane-1R-carboxylate was reacted with bromine to obtain a mixture of the A and B isomers of (R,S) α-cyano-3-phenoxybenzyl 2,2-dimethyl-3R-(1',2',2',2'-tetrabromomethyl)-cyclo-propane-1R-carboxylate.

I.R. Spectrum (chloroform)

Absorptions at 1740,1586 and 1485 cm$^{-1}$

RMN spectrum peaks at 1.20–1.26–1.35 ppm (hydrogens of 2-methyl of cyclopropane); at 4.3–4.48–4.67 ppm (hydrogen in the 1'-position of the side chain on cyclopropane); at 6.48 ppm (hydrogen fixed to same carbon as C=N); and at 6.97 to 7.17 ppm (hydrogens of aromatic ring).

EXAMPLE 5

(R,S) α-cyano-3-phenoxy-benzyl 2,2-dimethyl-3R-(2',2'-dichloro-1',2'-dibromoethyl)-cyclopropane-1R-carboxylate Using the procedure of Example 1, (R,S)α-cyano-3-phenoxy-benzyl 2,2-dimethyl-3S-(2',2'-dichlorovinyl)-cyclopropane-1R-carboxylate and bromine were reacted to form a mixture of the A and B isomers of (R,S) α-cyano-3-phenoxybenzyl 2,2-dimethyl-3R-(2',2'-dichloro-1',2'-dibromoethyl)-cyclopropane-1R-carboxylate.

I.R. Spectrum (chloroform)

Absorption at 1743, 1588 and 1487 cm$^{-1}$

RMN Spectrum peaks at 1.20–1.26–1.32–1.35 ppm (hydrogens of 2-methyl of cyclopropane); at 1.68–1.77 ppm (hydrogen in 1-position of cyclopropane); at 1.95–2.42 ppm (hydrogen of 3-position of cyclopropane); at 4.23–4.25–4.40–4.42–4.57 ppm (hydrogens in 1'-position of 3-ethyl chain of cyclopropane); at 6.48 ppm (hydrogen fixed to same carbon as —CN); and at 7.0 to 7.67 ppm (hydrogen of aromatic ring).

EXAMPLE 6

(S) 1-oxo-2-allyl-3-methyl-cyclopent-2-en-4-yl 2,2-dimethyl-3R-(1',2',2',2'-tetrabromoethyl)-cyclopropane-1R-carboxylate

STEP A:
2,2-dimethyl-3R-(1',2',2',2'-tetrabromoethyl)-cyclopropane-1R-carboxylic acid Using the procedure of Step A of Example 3, 2,2-dimethyl-3S-(2',2'-dibromovinyl)-cyclopropane-1R-carboxylic acid was brominated to form a mixture of the A and B isomers of 2,2-dimethyl-3R-(1',2',2',2'-tetrabromoethyl)-cyclopropane-1R-carboxylic acid.

RMN Spectrum peaks at 1.30 to 1.40 ppm (hydrogens of 2-methyls on cyclopropane); at 1.65–1.74 and 1.97 to 2.37 ppm (hydrogens at 1-and 3-positions of cyclopropane); at 4.30–4.47 and 4.47–4.65 ppm (hydrogen in 1'-position of ethyl); and at 9.63 ppm (carboxyl hydrogen).

STEP B:
2,2-dimethyl-3R-(1',2',2',2'-tetrabromoethyl)-cyclopropane-1R-carboxylic acid chloride Using the procedure of Step B of Example 3, the product of Step A was reacted with thionyl chloride to obtain 2,2-dimethyl-B 3R-(1',2',2,2-tetrabromoethyl)-cyclopropane-1R-carboxylic acid chloride which was used as is for the next step.

I.R. Spectrum (chloroform)

Absorption at —1778 cm$^{-1}$

STEP C: (S) 1-oxo-2-allyl-3-methyl-cyclopent-2-en-4-yl 2,2-dimethyl-3R-1',2',2',2'-tetrabromoethyl)-cyclopropane-1R-carboxylate (S)1-oxo-2-allyl-3-methoxy-cyclopent-2-en-4-ol in benzene was stirred under an inert atmosphere at 20° C. for 15 hours with the product of Step B in the presence of pyridine. Water was added thereto and the organic phase was decanted. The aqueous phase was extracted with benzene and the combined benzene phase were washed with water, sodium bicarbonate solution and then water 1 N hydrochloric acid and finally with water. The benzene phase was dried and evaporated to dryness under reduced pressure. The residue was chromatographed over sila gel and was eluted to obtain a mixture of the A and B isomers of (S) 1-oxo-2-allyl-3-methylcyclopent-2-en-4-yl 2,2-dimethyl-3R-(1',2',2',2'-tetrabromoethyl)-cyclopropane-1R-carboxylate.

I.R. Spectrum (chloroform)

Absorptions at 1725, 1710, 1655, 1638, 995 and 918 cm$^{-1}$

RMN Spectrum peaks at 1.30–1.32–1.36 ppm (hydrogens of 2-methyls of cyclopropane); at 1.98–2.05 (hydrogens at 3-methyl on cyclopropane at 4.83–5.25 ppm hydrogens of terminal methylene of allylic chain of allethrolone); at 4.30–4.48 and 4.43–4.67 ppm (hydrogens of lateral 3-ethyl on cyclopropane); and at 5.33–6.17 ppm (hydrogens on 2'-position of allyl of allethrolone).

EXAMPLE 7

A and B isomers of 5-benzyl-3-furyl-methyl 2,2-dimethyl-3S-(1',2',2',2'-tetrabromoethyl)-cyclopropane-1R-carboxylate Using the procedure of Step C of Example 6, the acid chloride of Step B of Example 3 was reacted with 5-benzyl-3-furyl-methanol in the presence of pyridine to obtain isomers A and B of 5-benzyl-3-furyl-methyl 2,2-dimethyl-3S-(1',2',2',2'-tetrabromoethyl)-cyclopropane-1R-carboxylate with a specific rotation of $[\alpha]_D = -104°$ and $+84°$ (c=0.5% in benzene), respectively. The A isomer was the more mobile in thin layer chromatography.

Characteristics of A isomer

RMN Spectrum peaks at 1.23–1.37 ppm (hydrogens of 2-methyls of cyclopropane) at 1.65–2.03 ppm (hydrogens in 1- and 3-positions of cyclopropane); at 3.92 ppm (hydrogens of methylene of benzyl); at 4.92 ppm (hydrogens of methylene of —COO—CH$_2$—);

at 5.27–5.67 ppm (hydrogen in 1'-position of 3-ethyl of cyclopropane); at 5.96 ppm (4-hydrogen of furyl); at 7.25 ppm hydrogens of phenyl) and at 7.33 ppm (2-hydrogen of furyl).

Circular dichroism (dioxane)

$\Delta^\epsilon = -6.5$ at 217 nm

Characteristics of B isomer

RMN Spectrum peaks at 1.20–1.42 ppm (hydrogens of 2-methyls of cyclopropane), at 1.67 to 2.17 ppm (hydrogens in 1- and 3-positions of cyclopropane); at 3.92 ppm (hydrogens of methyl of benzyl); at 4.95 ppm (hydrogens of methylene of COOCH$_2$); at 4.95 to 5.18 ppm (hydrogens in 1'-position of 3-ethyl of cyclopropane); at 7.25 ppm (hydrogens of aromatic ring of benzyl); and at 7.33 ppm (2-hydrogen of furyl).

Circular dichroism (dioxane)

$\Delta^\epsilon = +4.30$ at 247 nm

EXAMPLE 8

A and B isomers of (S) allethrolone 2,2-dimethyl-3S-(1',2',2',2'-tetrabromoethyl)-cyclopropane-1R-carboxylate Using the procedure of Step C of Example 6, the acid chloride of Step B of Example 3 was reacted with (S) allethrolone in the presence of pyridine to obtain the A and B isomers of (S) allethrolone 2,2-dimethyl-3S-(1',2',2',2'-tetrabromoethyl)-cyclopropane-1R-carboxylate with a specific rotation of $[\alpha]_D = -56°$ and $+81°$ (c=0.6% in benzene), respectively. The A isomer was the more mobile in thin-layer chromatography.

Characteristics of A isomer

RMN Spectrum peaks at 1.28–1.39 ppm (hydrogens of 2-methyls of cyclopropane); at 1.96 ppm (hydrogens of 3-methyl of allethrolone); at 4.83–5.16 ppm (hydrogens of terminal methylene of allylic chain); and at 5.33 to 6.16 ppm (hydrogen in 1'-position of 3-ethyl of cyclopropane and 2'-hydrogen of allyl):

Circular dichroism (dioxane)

$\Delta^\epsilon = 1.84$ at 332 nm
$\Delta^\epsilon = 2.06$ at 320 nm
$\Delta^\epsilon = -19$ at 225 nm Characteristics of B isomer melting point of 110° C.

RMN spectrum peaks at 1.27–1.47 ppm (hydrogens of 2-methyls of cyclopropane); at 2.07 ppm (hydrogens of 3-methyl of allethrolone); at 4.83 to 5.33 ppm (hydrogen at 1'-position of lateral chain in 3-position of cyclopropane and hydrogens of 2'-methylene of allyl); at 5.5–6.16 ppm (hydrogens in 2'-position of allyl); and at 5.15 ppm (hydrogens of 4-position of allethrolone).

Circular dichroism (dioxane)

$\Delta^\epsilon = +2.46$ at 332 nm
$\Delta^\epsilon = +2.76$ at 320 nm
$\Delta^\epsilon = +3.79$ at 250 nm
$\Delta^\epsilon = -1.7$ at 225 nm

EXAMPLE 9

A and B isomers of 3-phenoxy-benzyl 2,2-dimethyl-3S-(1',2',2',2'-tetrabromoethyl)-cyclopropane-1R-carboxylate Using the procedure of Step C of Example 6, the acid chloride of Step B of Example 3 was reacted with 3-phenoxy benzyl alcohol in the presence of pyridine to form the mixture of the A and B isomers of 3-phenoxybenzyl 2,2-dimethyl-3S-(1',2',2',2'-tetrabromoethyl)-cyclopropane-1R-carboxylate with a specific rotation of $[\alpha]_D = -106°$ (c=0.5% in benzene) and +61.5° (c=2.3% in benzene), respectively. A isomer was the more mobile in thin-layer chromatography and melted at 90° C.

Characteristics of A isomer

RMN spectrum peaks at 0.92–1.37 ppm (hydrogens of 2-methyls of cyclopropane); at 1.67–2.08 ppm (hydrogens of 1- and 3-position of cyclopropane); at 5.08 ppm (hydrogens of methylene of —COOCH$_2$); at 5.38–5.56 ppm (1'-hydrogen of 3-ethyl of cyclopropane); and at 6.67 to 7.58 ppm (hydrogens of aromatic ring).

Circular dichroism (dioxane)

$\Delta^\epsilon = -10$ at 218 nm

Characteristics of B isomer

RMN Spectrum peaks at 1.22–1.42 ppm (hydrogen of 2-methyls of cyclopropane); at 1.67 to 2.08 ppm (1- and 3-hydrogens of cyclopropane); at 4.93 to 5.33 ppm (1'-hydrogen of 3-ethyl of cyclopropane); at 5.15 ppm (hydrogens of methylene of COOCH$_2$); and at 6.75 to 7.58 ppm (hydrogens of aromatic ring).

Circular dichorism (dioxane)

$\Delta^\epsilon = +4.6$ at 247 nm

EXAMPLE 10

(S) allethrolone 2,2-dimethyl-3R-(2',2'-dichloro-1',2'-dibromoethyl)-cyclopropane-1R-carboxylate

STEP A:

2,2-dimethyl-3R-(2',2'-dichloro-1',2'-dibromoethyl)-cyclopropane-1R-carboxylic acid Using the procedure of Step A of Example 3, 2,2-dimethyl-3S-(2',2'-dichlorovinyl)-cyclopropane-1R-carboxylic acid was brominated to obtain a mixture of A and B isomers of 2,2-dimethyl-3R-(2',2'-dichloro-1',2'-dibromoethyl)-cyclopropane-1R-carboxylic acid.

RMN Spectrum peaks at 1.17–1.37 ppm (hydrogens of 2-methyls of cyclopropane); from 1.65–1.73 ppm to 1.93–2.03 ppm (hydrogens in the 1-position of cyclopropane); and at 4.23–4.45 and at 4.45–4.62 ppm (1'-hydrogen of 3-ethyl of cyclopropane).

STEP B:

2,2-dimethyl-3R-(2',2'-dichloro-1',2'-dibromoethyl)-cyclopropane-1R-carboxylic acid chloride Using the procedure of Step B of Example 3, the product of Step A was reacted with thionyl chloride to obtain 2,2-dimethyl-3R-(2',2'-dichloro-1',2'-dibromoethyl)-cyclopropane-1R-carboxylic acid chloride.

I.R. Spectrum (chloroform)

Absorption at 1777 cm$^{-1}$

STEP C: (S) allethrolone 2,2-dimethyl-3R-(2',2'-dichloro-1',2'-dibromoethyl)-cyclopropane-1R-carboxylate Using the procedure of Step C of Example 6, the product of Step B was reacted with (S) allethrolone in the presence of pyridine to obtain a mixture of the A and B isomers of (S) allethrolone 2,2-dimethyl-3R-(2',2'-dichloro1',2'-dibromoethyl)-cyclopropane-1R-carboxylate.

RMN Spectrum peaks at 1.30–1.34 ppm (hydrogens of 2-methyls of cyclopropane); at 1.63–3.0 ppm (hydrogens in 1- and 3-position of cyclopropane); at 2.05 ppm (hydrogens of 3-methyl of allethrolone); at 1.95–3.03 ppm (hydrogens of 1'-methylene of allyl chain); at 4.25–4.43–4.61 ppm (1'-hydrogen of 3-ethyl of cyclopropane); at 4.25 ppm (hydrogens of terminal methylene of allyl chain); at 4.83–5.41 ppm (2'-hydrogen of allyl chain); and at 5.83 ppm (hydrogens in 4-position of allethrolone).

EXAMPLE 11

(RS)α-cyano-3-phenoxy-benzyl 2,2-dimethyl-3S-(2',2'-dibromo-1',2'-dichloroethyl)-cyclopropane-1R-carboxylate

STEP A: 2,2-dimethyl-3S-(1',2'-dichloro-2',2'-dibromoethyl)-cyclopropane-1R-carboxylic acid 11.8 g of chlorine were bubbled into 30 ml of carbon tetrachloride at $-15°$ C. and then a solution of 24 g of 2,2-dimethyl-3R-(2',2'-dibromovinyl)-cyclopropane-1R-carboxylic acid in 37 ml of carbon tetrachloride was slowly added thereto at $-10°$ C. The mixture was stirred for 90 minutes at $0°$ C. and 2 hours at $25°$ C. and was then evaporated to dryness under reduced pressure. The residue was crystallized from carbon tetrachloride to obtain 7.4 g of the A and B isomers of 2,2-dimethyl-3S-(1',2'-dichloro-2',2'-dibromoethyl)-cyclopropane-1R-carboxylic acid melting point of $134°$ C.

RMN Spectrum peaks at 1.32–1.44 ppm and at 1.28–1.48 ppm (hydrogens of 2-methyls of cyclopropane); at 5.08–5.45 and 4.67–5.0 ppm (1'-hydrogen of 3-ethyl of cyclopropane); and at 10.1 ppm (carboxyl hydrogen).

STEP B: 2,2-dimethyl-3S-(1',2'-dichloro-2',2'-dibromoethyl)-cyclopropane-1R-carboxylic acid chloride Using the procedure of Step B of Example 3, the product of Step A was reacted with thionyl chloride in the presence of pyridine to obtain 2,2-dimethyl-3S-(1',2'-dichloro-2',2'-dibromoethyl)-cyclopropane-1R-carboxylic acid chloride which was used as is for the next step.

STEP C: α-cyano-3-phenoxy-benzyl 2,2-dimethyl-3S-(1',2'-dichloro-2',2'-dibromoethyl)-cyclopropane-1R-carboxylate Using the procedure of Step C of Example 6, the product of Step B was reacted with α-cyano-3-phenoxy-benzyl alcohol in the presence of pyridine to obtain a mixture of the A and B isomers of α-cyano-3-phenoxy-benzyl 2,2-dimethyl-3S-(1',2'-dichloro-2',2'-dibromoethyl)-cyclopropane-1R-carboxylate.

RMN Spectrum peaks at 1.23–1.52 ppm (hydrogens of 2-methyls of cyclopropane); at 1.77 to 2.11 ppm (1-and 3-hydrogens of cyclopropane); at 4.72–4.88 and 5.02–5.21 ppm (1'-hydrogen of 3-ethyl of cyclopropane); at 6.40 to 6.43 ppm (hydrogen attached to same carbon as —CN); and at 6.94 to 7.66 ppm (hydrogens of aromatic ring).

EXAMPLE 12

(S) allethrolone 2,2-dimethyl-3S-(2',2'-dibromo-1',2'-dichloroethyl)-cyclopropane-1R-carboxylate Using the procedure of Step C of Example 6, the acid chloride of Step B of Example 11 was reacted with (S) allethrolone to obtain a mixture of the A and B isomers of (S) allethrolone 2,2-dimethyl-3S-(1',2'-dichloro-2',2'-dibromoethyl)-cyclopropane-1R-carboxylate.

RMN Spectrum peaks at 1.25–1.45 and 1.29–1.40 ppm (hydrogens of 2-methyl of cyclopropane); at 1.96 ppm (hydrogens of 3-methyl of allethrolone); at 2.96–3.03 ppm (hydrogens of 1'-methylene of allyl chain); at 4.83–5.16 ppm (hydrogens of terminal methylene of allyl chain); at 5.25–5.36 ppm (1'-hydrogen of 3-ethyl of cyclopropane); and at 5.5 to 6.0 ppm (4-hydrogens of allethrolone and 2'-hydrogen of allyl chain).

EXAMPLE 13

(R,S)α-cyano-3-phenoxy-benzyl 2,2-dimethyl-3R-(1',2'-dichloro-2',2'-dibromoethyl)-cyclopropane-1R-carboxylate Using the process of Step C of Example 6, the acid chloride of Step B of Example 10 was reacted with (R,S)α-cyano-3-phenoxy-benzyl alcohol to obtain a mixture of the A and B isomers of (R,S)α-cyano-3-phenoxy-benzyl 2,2-dimethyl-3R-(1',2'-dichloro-2',2'-dibromoethyl)-cyclopropane-1R-carboxylate

RMN Spectrum:

peaks at 1.22–1.27–1.37–1.4–1.45 ppm (hydrogens of 2-methyls of cyclopropane); at 1.67–2.5 ppm (1- and 3-hydrogen of cyclopropane); at 3.67–4.5 ppm (1'-hydrogen of 3-ethyl of cyclopropane); at 6.52 ppm (hydrogen attached to same carbon as —CN); and at 7.0–7.67 ppm (hydrogens of aromatic ring).

EXAMPLE 14

(S) allethrolone 2,2-dimethyl-3R-(1',2'-dibromo-2',2'-difluoroethyl)-cyclopropane-1R-carboxylate

STEP A: 2,2-dimethyl-3R-(1',2'-dibromo-2',2'-difluoroethyl-cyclopropane-1R-carboxylic acid Using the procedure of Step A of Example 3, 2,2-dimethyl-3R-(2',2'-difluorovinyl)-cyclopropane-1R-carboxylic acid was reacted with bromine at $-60°$ C. to obtain a mixture of the A and B isomers of 2,2-dimethyl-3R-(1',2'-dibromo-2',2'-difluoroethyl)-cyclopropane-1R-carboxylic acid melting at $122°$ C.

RMN Spectrum:

peaks at 1.33–1.36 ppm (hydrogens of 2-methyls of cyclopropane); at 1.60–2.23 ppm (1- and 3-hydrogens of cyclopropane); at 3.75–4.37 ppm (1'-hydrogen of 3- ethyl of cyclopropane); and at 10.96 ppm (carboxyl hydrogen).

STEP B:
2,2-dimethyl-3R-(1',2'-dibromo-2',2'-difluoroethyl)cyclopropane-1-carboxylic acid chloride Using the procedure of Step B of Example 3, the product of Step A was reacted with thionyl chloride to form 2,2-dimethyl-3R-(1',2'-dibromo-2',2'-difluoroethyl)-cyclopropane-1R-carboxylic acid chloride which was used as is for the next step.

STEP C: (S) allethrolone 2,2-dimethyl-3R-(1',2'-dibromo-2',2'-difluoroethyl)-cyclopropane-1R-carboxylate Using the procedure of Step C of Example 6, the acid chloride of Step B was reacted with (S) allethrolone in the presence of pyridine to obtain a mixture of the A and B isomers of (S) allethrolone 2,2-dimethyl-3R-(1',2'-dibromo-2',2'-difluoroethyl)-cyclopropane-1R-carboxylate.

RMN Spectrum peaks at 1.32 ppm (hydrogens of 2-methyls of cyclopropane); at 3.26–1.68 and 1.73 to 2.19 ppm (1-hydrogens of cyclopropane); at 1.20 ppm (hydrogens of 3-methyl of allethrolone); at 2.93–3.05 ppm (hydrogens of 1'-methylene of allyl chain); at 4.83–5.25 ppm (hydrogens of terminal methylene of allyl chain); at 3.58–4.33 ppm (1'-hydrogen of 3-ethyl of cyclopropane); peaks at 4.83–5.25 ppm (2'-hydrogen of allyl chain); and at 5.83 ppm (4-hydrogens of allethrolone).

EXAMPLE 15

(R,S)α(-cyano-3-phenoxy-benzyl 2,2-dimethyl-3S-(1',2'-dibromo-2',2'-dichloroethyl)-cyclopropane-1R-carboxylate STEP A:
2,2-dimethyl-3S-(1',2'-dibromo-2',2'-dichloroethyl)-cyclopropane-1R-carboxylic acid Using the procedure of Step A of Example 3, 2,2-dimethyl-3R-(2',2'-dichlorovinyl)-cyclopropane-1R-carboxylic acid was reacted with bromine to obtain a mixture of the A and B isomers of 2,2-dimethyl-3S-(1',2'-dibromo-2',2'-dichloroethyl)-cyclopropane-1R-carboxylic acid.

RMN Spectrum peaks at 1.26–1.30 and at 1.41–1.42 ppm (hydrogens of 3-methyls of cyclopropane); at 1.83–2.17 ppm (1- and 3-hydrogens of cyclopropane); at 4.83–5.58 ppm (1'-hydrogen of 3-ethyl of cyclopropane); and at 8.17 ppm (carboxyl hydrogen).

STEP B:
2,2-dimethyl-3S-(1',2'-dibromo-2',2'-dichloroethyl)-cyclopropane-1R-carboxylic acid chloride Using the procedure of Step B of example 3, the product of Step A was reacted with thionyl chloride to obtain 2,2-dimethyl-3S-(1',2'-dibromo-2',2'-dichloroethyl)-cyclopropane-1-R-carboxylic acid chloride which was used as is for the next step.

STEP C: (R,S)α-cyano-3-phenoxy-benzyl 2,2-dimethyl-3S-(1',2'-dibromo-2',2'-dichloroethyl)-cyclopropane-1R-carboxylate Using the procedure of Step C of Example 6, the product of Step B was reacted with (RS)α-cyano-3-phenoxy-benzyl alcohol to obtain a mixture of the A and B isomers of (R,S)α-cyano-3-phenoxy-benzyl 2,2-dimethyl-3S-(1',2'-dibromo-2',2'-dichloroethyl)-cyclopropane-1R-carboxylte

EXAMPLE 16

(R,S)α-cyano-3-phenoxy-benzyl 2,2-dimethyl-3S-(1',2',2',2'-tetrabromoethyl)-cyclopropane-1R-carboxylate STEP A:
2,2-dimethyl-3S-(1',2',2',2'-tetrabromoethyl)-cyclopropane-1R-carboxylate acid A solution of 0.9 ml of bromine in 10 ml of carbon tetrachloride was added over 30 minutes to a mixture of 5 g of 2,2-dimethyl-3R-(2',2'-dibromovinyl)-cyclopropane-1R-carboxylic acid in 30 ml of carbon tetrachloride and the mixture was stirred for 90 minutes and was evaporated to dryness under reduced pressure to obtain 8.9 g of raw 2,2-dimethyl-3S-(1',2',2',2'-tetrabromoethyl)-cyclopropane-1R-carboxylic acid.

STEP B:
2,2-dimethyl-3S-(1',2',2',2'-tetrabromoethyl)-cyclopropane-1R-carboxylic acid chloride 8.9 g of 2,2-dimethyl-3S-(1',2',2',2'-tetrabromoethyl)-cyclopropane-1R-carboxylic acid were added to a mixture of 40 ml of petroleum ether (b.p. =35°–70° C.) and 10 ml of thionyl chloride and the mixture was refluxed for 3 hours and the mixture was evaporated to dryness to obtain the raw 2,2-dimethyl-3S-(1',2',2',2'-tetrabromoethyl)-cyclopropane-1R-carboxylic acid chloride which was used as is for the next step.

STEP C: (R,5)α-cyano-3-phenoxy-benzyl 2,2-dimethyl-3S-(1',2',2',2'-tetrabromoethyl)-cyclopropane-1R-carboxylate A solution of the product of Step B in 40 ml of benzene was added over 15 minutes at 0° C. to a mixture of 7 g of (RS) α-cyano-3-phenoxy-benzyl alcohol in 5 ml of benzene and 10 ml of pyridine and the mixture was stirred at 20° C. for 16 hours and was then acidified to a pH of 1 with aqueous dilute hydrochloric acid. The mixture was extracted with benzene and the organic phase was washed with water, dried over magnesium sulfate and evaporated to dryness. The residue was chromatographed over silica gel and was eluted with benzene to obtain 7.33 g of (RS) α-cyano-3-phenoxy-benzyl 2,2-dimethyl-3S-(1',2',2',2'-tetrabromoethyl)-cyclopropane-1R-carboxylate.

Analysis: $C_{22}H_{19}O_5NBr_4$; molecular weight=665.05 Calculated: %C: 39.73; %H: 2.88; %N: 2.10; %Br 48.06; Found: %C: 39.7; %H: 3; %N: 2.2; %Br 47.4.

I.R. Spectrum (chloroform)

Absorption at 1743 cm$^{-1}$ ($>$C=0); at 1613, 1588 and 1477 cm$^{-1}$ (aromatic ring).

U.V. Spectrum (ethanol):
Inflex. towards 230 nm $E_1^1$=194
Inflex. towards 270 nm $E_1^1$=36
Max. at 278 nm $E_1^1$=37
Inflex. towards 285 nm $E_1^1$=28

RMN Spectrum (deuterochloroform)

peaks at 1.23–1.5 ppm (hydrogens of geminal methyls); at 1.83–2.16 ppm (hydrogens of cyclopropane); at 4.82–5.5 ppm (1'-hydrogen of 3-ethyl of cyclopropane);

at 6.37–6.42 ppm (hydrogen attached to same carbon as -CN); and at 6.83–7.58 ppm (hydrogens of aromatic ring).

EXAMPLE 17

3-phenoxy-benzyl 2,2-dimethyl-3R-(1',2',2',2'-tetrabromoethyl)-cyclopropane-1R-carboxylate STEP A: 2,2-dimethyl-3R-(1',2',2',2'-tetrabromoethyl)-cyclopropane-1R-carboxylic acid Using the procedure of Step A of Example 16, 2,2-dimethyl-3S-(2',2'-dibromovinyl)-cyclopropane-1R-carboxylic acid was reacted with bromine to obtain a mixture of A and B isomers of 2,2-dimethyl-3R-(1',2',2',2'-tetrabromoethyl)cyclopropane-1R-carboxylic acid.

RMN Spectrum (deuterochloroform)

peaks at 1.30–1.40 ppm (hydrogens of 2-methyls of cyclopropane); at 1.65–1.74 and 1.97–2.37 ppm (1- and 3-hydrogens of cyclopropane); at 4.30–4.47 and at 4.47–4.65 ppm of (1'-hydrogen of 3-ethyl of cyclopropane); and at 9.63 ppm (carboxyl hydrogen).

STEP B: 2,2-dimethyl-3R-(1',2',2',2'-tetrabromoethyl)-cyclopropane-1R-carboxylic acid chloride Using the procedure of Step B of Example 16, the product of Step A was reacted with thionyl chloride to obtain 2,2-dimethyl-3R-(1',2',2',2'-tetrabromoethyl)-cyclopropane-1R-carboxylic acid chloride which was used as is for the next step.

STEP C: 3-phenoxy-benzyl 2,2-dimethyl-3R-(1',2',2',2'-tetrabromoethyl)-cyclopropane-1R-carboxylate 2.4 g of 3-phenoxy-benzyl alcohol were added at 0° C. to a solution of 5 g of the product of Step B in 20 ml of benzene and then 4 ml of pyridine were progressively added thereto. The mixture was stirred at 20° C. for 48 hours and was then poured into an aqueous hydrochloric acid solution. The mixture was extracted with benzene and the benzene extract was washed with aqueous sodium bicarbonate solution, with water, dried over sodium sulfate and concentrated to dryness under reduced pressure to obtain 6.2 g of residue which was chromatographed over silica gel. Elution with 9-1 petroleum ether (b.p. = 35°–75° C.)-ethyl ether mixture yielded 3.68 g of a mixture of the A and B isomers of 3-phenoxy-benzyl 2,2-dimethyl-3R-(1',2',2',2'-tetrabromoethyl)cyclopropane-1R-carboxylate.

Analysis: $C_{21}H_{20}Br_4O_3$; molecular weight = 640.03 Calculated: %C: 39.41; %H: 3.15; %Br 49.94; Found: %C: 39.9; %H: 3.2; %Br 50.2.

I.R. Spectrum (chloroform)

Absorption at 1728 cm$^{-1}$ (carbonyl) and at 1615, 1590 and 1490 cm$^{-1}$ (aromatic ring).

RMN Spectrum (deuterochloroform)

peaks at 1.26–1.29–1.35 ppm (hydrogens of geminal methyls); at 2.00–2.33 ppm (1-hydrogen of cyclopropyl); at 1.70–1.79 ppm (3-hydrogen of cyclopropyl); at 4.31–4.48–4.50–4.67 ppm (1'-hydrogen of 3-ethyl of cyclopropane); at 5.17–5.20 ppm (hydrogens of methylene of benzyl); and at 6.92–7.58 ppm (hydrogens of aromatic ring).

EXAMPLE 18

3-phenoxy-benzyl 2,2-dimethyl-3S-(1',2',2',2'-tetrachloroethyl)-cyclopropane-1R-carboxylate STEP A: 2,2-dimethyl-3S-(1',2',2',2'-tetrachloroethyl)-cyclopropane-1R-carboxylic acid 11.8 g of chlorine were dissolved in 30 ml of carbon tetrachloride and then a solution of 16.7 g of 2,2-dimethyl-3R-(2',2'-dichlorovinyl)-cyclopropane-1R-carboxylic acid in 40 ml of methylene chloride was added thereto at 0° C. The mixture was stirred at 0° C. for 24 hours and then at 25° C. for 3 hours and the excess chlorine was removed by bubbling nitrogen through the mixture. The mixture was evaporated to dryness under reduced pressure and the residue was chromatographed over silica gel. Elution with an 8-2 cyclohexaneethyl acetate mixture yielded a product which was crystallized from petroleum ether (b.p. = 35°–75° C.) to obtain 3.14 g of 2,2-dimethyl-3S-(1',2',2',2'-tetrachloroethyl)-cyclopropane-1R-carboxylic acid melting at 144° C.

Analysis: $C_9H_{10}Cl_4O_2$; molecular weight = 279.98 Calculated: %C: 34.3; %H: 3.6; %Cl: 50.6; Found: %C: 34.4; %H: 3.7; %Cl: 50.3.

RMN Spectrum (deuterochloroform)

peaks at 1.26–1.42 ppm and 1.30–1.42 ppm (hydrogens of geminal methyls); at 4.67–5.17 ppm and 5.08–5.43 ppm (1'hydrogen of 3-ethyl of cyclopropane); at 1.67–2.00 ppm of (1- and 3-hydrogens of cyclopropane); and at 10.2 ppm (carboxyl hydrogen).

STEP B: 2,2-dimethyl-3S-(1',2',2',2'-tetrachloroethyl)cyclopropane-1R-carboxylic acid chloride A mixture of 6.75 g of the product of Step A in 60 ml of petroleum ether (b.p. = 35°–70° C.) and 8.7 ml of thionyl chloride was refluxed for 4½ hours and was then evaporated to dryness under reduced pressure. The residue was added to benzene and the solution was evaporated to dryness to obtain raw 2,2-dimethyl-3S-(1',2',2',2'-tetrachloroethyl)-cyclopropane-1R-carboxylic acid chloride which was used as for the next step.

STEP C: 3-phenoxy-benzyl 2,2-dimethyl-3S-(1',2',2',2'-tetrachloroethyl)-cyclopropane-1R-carboxylate A solution of 5.2 g of 3-phenoxy-benzyl alcohol in 50 ml of benzene was added at 75° C. to a solution of the product of Step A in 60 ml of benzene followed by the addition of 2.6 ml of pyridine and stirring for 16 hours at 20° C. The reaction mixture was poured into a water-hydrochloric acid mixture and the mixture was extracted with ethyl ether. The ether extracts were evaporated to dryness to obtain 11 g of residue which was chromatographed over silica gel. Elution with a 1-1 benzene-cyclohexane mixture and crystallization from ether gave a first fraction of 4.6 g of 3-phenoxybenzyl 2,2-dimethyl-3S-(1',2',2',2'-tetrachloroethyl)-cyclopropane-1R-carboxylate with a melting point of 86° C. and a specific rotation of $[\alpha]_D^{20} = -86.5°$ (c = 0.5% in benzene).

Analysis: $C_{21}H_{20}Cl_4O_3$; molecular weight = 462.20 Calculated: %C: 54.56; %H: 4.35; %Cl 30.68; Found: %C: 54.9; %H: 4.5; %Cl: 30.3.

U.V. Spectrum (ethanol)

Inflex. towards 226 nm $E_1^1 = 228$
Inflex. towards 266 nm $E_1^1 = 36$
Max. at 271 nm $E_1^1 = 41$
Max. at 277 nm $E_1^1 = 40$ RMN Spectrum (deuterochloroform)

peaks at 1.27–1.4 ppm (hydrogens of geminal methyls of isomer A); at 5.13 ppm (hydrogens of

of isomer A); at 5.27–5.43 ppm (1'-hydrogen of 3-ethyl of isomer A); at 1.23–1.40 ppm (hydrogens of geminal methyls of isomer B); at 5.18 ppm (hydrogens of

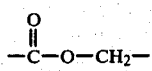

of isomer B); at 4.83–5.17 ppm (1' hydrogen of 3-ethyl of isomer B); at 1.61–2.03 ppm (1- and 3-hydrogens of cyclopropane); and at 6.92–7.58 ppm (hydrogens of aromatic ring). The said spectrum showed that the product was about 90% of isomer A and about 10% of isomer B.

Chromatography of the product and crystallization from ether yielded a second fraction of 3.3 g of 3-phenoxybenzyl 2,2-dimethyl-3S-(1',2',2',2'-tetrachloroethyl)-cyclopropane-1R-carboxylate with a melting point of 62° C. and a specific rotation $[\alpha]_D^{20} = -9°$ (c = 1% in benzene) and the RMN spectrum showed the product to be about 60% isomer B and about 40% of isomer A.

I.R. Spectrum (chloroform)

Absorption at 1725 cm$^{-1}$ (carbonyl) and at 1615, 1590 and 1490 cm$^{-1}$ (aromatic ring).

RMN Spectrum (deuterochloroform)

peaks at 1.23–1.41 ppm (hydrogens of geminal methyls of isomer B); at 4.83–5.17 ppm (1'-hydrogen of 3-ethyl of isomer B); at 5.2 ppm (hydrogens of

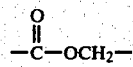

of isomer B); at 1.28–1.4 ppm (hydrogens of geminal methyls of isomer A); at 5.27–5.43 ppm (1'-hydrogen of 3-ethyl of isomer A); at 5.13 ppm (hydrogens of

of isomer A); at 1.58–2.08 ppm (1- and 3-hydrogens of cyclopropane); and at 6.9–7.16 ppm (hydrogens of aromatic ring).

EXAMPLE 19

(R,S) α-cyano-3-phenoxy-benzyl 2,2-dimethyl-3S-(1',2',2',2'-tetrachloroethyl)-cyclopropane-1R-carboxylate A solution of 4.6 g of R,S, α-cyano-3-phenoxy-benzyl alcohol in 30 ml of benzene was added at 5° C. to a solution of 2,2-dimethyl-3S-(1',2',2',2'-tetrachloroethyl)-cyclopropane-1R-carboxylic acid chloride [prepared from 5.4 g of the corresponding acid as in Step B of Example 18] in 50 ml of benzene and after adding 2.2 ml of pyridine, thereto, the mixture was stirred for 48 hours at room temperature and was poured into aqueous hydrochloric acid solution. The mixture was extracted with ether and the extracts were evaporated to dryness. The residue was chromatographed over silica gel and was eluted with a 1–2 benzene-cyclohexane mixture to obtain 4.7 g of (R,S) α-cyano-3-phenoxy-benzyl 2,2-dimethyl-3S-(1',2',2',2'-tetrachloroethyl)-cyclopropane-1R-carboxylate with a specific rotation of $[\alpha]_d^{20} = -56.5°$ (c = 0.4% in benzene).

Analysis: $C_{22}H_{19}Cl_4NO_3$; molecular weight = 487.22 Calculated: %C: 54.23; %H: 3.93; %N: 2.87; %Cl: 29.11; Found: %C: 54.3; %H: 3.8; %N: 2.8; %Cl: 29.0.

U.V. Spectrum (ethanol)

Inflex. towards 227 nm $E_1^1 = 225$
Infex. towards 268 nm $E_1^1 = 35$
Infex. towards 272 nm $E_1^1 = 38$
Max. at 278 nm $E_1^1 = 43$
Inflex. towards 284 nm $E_1^1 = 33$ RMN Spectrum (deuterochloroform)

peaks at 1.22–1.43 ppm (hydrogens of geminal methyls); at 1.67–2.08 ppm (1- and 3-hydrogens of cyclopropane); at 4.83–6.47 ppm (1'-hydrogen of 3-ethyl of cyclopropane); at 6.38–6.46 ppm (hydrogen or same carbon as —CN); and at 6.92–7.58 ppm (hydrogens of aromatic ring).

EXAMPLE 20

(R,S) allethrolone 2,2-dimethyl-3S-(1',2',2',2'-tetrachloroethyl)-cyclopropane-1R-carboxylate A solution of 4 g of (R,S) allethrolone in 15 ml of benzene was added at 5° C. to a solution of 2,2-dimethyl-3S-(1',2',2',2'-tetrachloroethyl)-cyclopropane-1R-carboxylic acid chloride (produced from 7 g of the corresponding acid by Step B of Example 18) in 20 ml of benzene and after the addition of 2.55 ml of pyridine thereto, the mixture was stirred for 18 hours at 20° C. and was poured into aqueous hydrochloric acid. The mixture was extracted with ether and the ether extracts were evaporated to dryness. The residue was chromatographed over silica gel and was eluted with a 9-1 cyclohexane-ethyl acetate mixture to obtain 8 g of (R,S) allethrolone 2,2-dimethyl-3S-(1',2',2',2'-tetrachloroethyl)cyclopropane-1R-carboxylate with a specific rotation of $[\alpha]_d^{20} = -54.7°$ (c = 0.5% in benzene).

Analysis: $C_{17}H_{20}Cl_4O_3$; molecular weight = 414.15 Calculated %C: 49.30; %H: 4.87; %Cl: 34.24; Found: %C: 49.5; %H: 4.9; %Cl: 34.1.

U.V. Spectrum (ethanol) Max. at 227 nm $E_1^1 = 334$

RMN Spectrum (deuterochloroform)

peaks at 1.31–1.42 ppm (hydrogens of geminal methyls); at 1.62–2.17 ppm (1- and 3-hydrogens of cyclopropane); and at 4.83–6.17 ppm (1-hydrogen of 3-ethyl of cyclopropane).

EXAMPLE 21

(R,S) α-cyano-3-phenoxy-benzyl 2,2-dimethyl-3R-(1',2',2',2'-tetrachloroethyl)-cyclopropane-1R-carboxylate

STEP A:
2,2-dimethyl-3R-(1',2',2',2'-tetrachloroethyl)-cyclopropane-1R-carboxylic acid A solution of 18.8 g of 2,2-dimethyl-3S-(2',2'-dichlorovinyl)-cyclopropane-1R-carboxylic acid in 30 ml of methylene chloride was added over 15 minutes at −10° C. to a solution of 13.25 g of chlorine in 30 ml of carbon tetrachloride and the resulting mixture was passed over a refrigerant in which circulated a liquid at −60° C. to condense the nonreacted chlorine. The mixture was stirred at −10° C. for 90 minutes and then for 90 minutes at 0° C. and excess chlorine was removed at 20° C. by bubbling nitrogen therethrough. The mixture was evaporated to dryness under reduced pressure and the residue was chromatographed over silica gel. Elution with a 7-3 cyclohexane-ethyl acetate mixture yielded 23 g of 2,2-dimethyl-3R-(1',2',2',2'-tetrachloroethyl)-cyclopropane-1R-carboxylic acid which was used as is for the next step.

STEP B:
2,2-dimethyl-3R-(1',2',2',2'-tetrachloroethyl)-cyclopropane-1R-carboxylic acid chloride 12.276 g of the product of Step A were added to a mixture of 30 ml of petroleum ether (b.p.=35°–75° C.) and 16 ml of thionyl chloride and the mixture was refluxed for 4½ hours and was then evaporated to dryness under reduced pressure. The residue was taken up in benzene and the solution was evaporated to dryness to obtain 2,2-dimethyl-3R-(1',2',2',2'tetrachloroethyl)-cyclopropane-1R-carboxylic acid chloride which was used as is for the next step.

STEP C: (R,S) α-cyano-3-phenoxy-benzyl 2,2-dimethyl-3B-(1',2',2',2'-tetrachloroethyl)-cyclopropane-1R-carboxylate A solution of 10.5 g of (R,S) α-cyano-3-phenoxybenzyl alcohol in 20 ml of benzene was rapidly added at 5° C. to a mixture of the product of Step B in 25 ml of benzene and 4.5 ml of pyridine were rapidly added thereto. The mixture was stirred at 20° C. for 16 hours and was poured into a mixture of ice-water-hydrochloric acid. The mixture was extracted with ethyl ether and the organic phase was washed with water, dried and evaporated to dryness under reduced pressure. The residue was chromatographed over silica gel and was eluted with a 9-1 cyclohexane-ethyl acetate mixture to obtain 14.18 g of (R,S) α-cyano-3-phenoxybenzyl 2,2-dimethyl-3R-(1',2',2',2'-tetrachloroethyl)-cyclopropane-1R-carboxylate with a specific rotation of $[\alpha]_D^{20} = -22.5°$ (c=0.5% in benzene).

Analysis: $C_{22}H_{19}Cl_4NO_3$; molecular weight=487.21
Calculated: %C: 54.2; %H 3.9; %Cl: 29.1; %N 2.9
Found: %C: 54.0; %H: 4.0; %Cl: 29.0; %N: 2.7.

I.R. Spectrum (chloroform)

Absorptions at 1742 cm$^{-1}$ (carbonyl) and at 1610, 1584 and 1484 cm$^{-1}$ (aromatic ring).

U.V. Spectrum (ethanol)

Infex. at 230 nm $E_1^1 = 230$
Infex. at 267 nm $E_1^1 = 41$
Infex. at 271 nm $E_1^1 = 44$
Max. at 277 nm $E_1^1 = 49$
Infex. at 283 nm $E_1^1 = 37$
Infex. at 305 nm $E_1^1 = 4$ RMN Spectrum (deuterochloroform):

peaks at 1.22–1.42 ppm (hydrogens of methyl); at 1.50–2.50 ppm (1- and 3-hydrogens at cyclopropane); at 3.66–4.41 ppm (1'-hydrogen at 3-ethyl of cyclopropane); at 6.5 ppm (hydrogen on same carbon as —CN); and at 7.00–7.66 ppm (hydrogens of aromatic ring).

EXAMPLE 22

3-phenoxy-benzyl 2,2-dimethyl-3R-(1',2',2',2'-tetrachloroethyl)-cyclopropane-1R-carboxylate A solution of 4 g of 3-phenoxy-benzyl alcohol in 15 ml of benzene was added at 0° C. to 18.6 ml of a solution of the the acid chloride in 30 ml of benzene prepared from 10.4 g of 2,2-dimethyl-3R-(1',2',2',2'-tetrachloroethyl)cyclopropane-1R-carboxylic acid and after the addition of 2 ml of pyridine thereto, the mixture was stirred at 20° C. for 18 hours and was poured into a mixture of ice, water and hydrochloric acid. The mixture was extracted with ethyl ether and the extracts were washed with water, dried over magnesium sulfate, filtered and evaporated to dryness under reduced pressure. The 8.6 g of residue was chromatographed over silica gel and was eluted with a 95-5 cyclohexane-ethyl acetate mixture and then a 1-1 cyclohexane-benzene mixture to obtain 3-phenoxy-benzyl 2,2-dimethyl-3R-(1',2',2',2'-tetrachloroethyl)-cyclopropane-1R-carboxylate.

Analysis: $C_{21}H_{20}Cl_4O_3$; molecular weight=462.20
Calculated: %C: 54.6; %H: 4.4; %Cl: 30.7; Found: %C: 55.2; %H: 4.5; %Cl: 29.4.

I.R. Spectrum (chloroform)

Absorption at 1728 cm$^{-1}$ (carbonyl) and at 1615 and 1587 cm$^{-1}$ (aromatic ring).

U.V. Spectrum (ethanol)

Inflex. at 227 nm $E_1^1 = 245$
Inflex. at 266 nm $E_1^1 = 36$
Max. at 272 nm $E_1^1 = 42$
Max. at 277 nm $E_1^1 = 40$ RMN Spectrum (deuterochloroform)

peaks at 1.19–1.33 ppm (hydrogens of geminal methyls); at 1.66–2.25 ppm (1- and 3-hydrogens of cyclopropane); 4.0–4.41 ppm (1'-hydrogen of 3-ethyl of cyclopropane); at 5.18 ppm (methylene of benzyl); and at 6.83–7.67 ppm (hydrogens of aromatic ring).

EXAMPLE 23

(S) allethrolone 2,2-dimethyl-3R-(1',2',2',2'-tetrachloroethyl)-cyclopropane-1R-carboxylate The acid chloride prepared from 10.4 g of 2,2-dimethyl-3R-(1',2',2',2'-tetrachloroethyl)-cyclopropane-1R-carboxylic acid by the procedure of Step B of Example 21 was dissolved in 30 ml of benzene to obtain a final solution of 37.2 ml to which a solution of 3.2 g of (S) allethrolone in 15 ml of benzene was added at 0° C. 2 ml of pyridine were added thereto with stirring and the mixture was stirred at 20° C. for 16 hours and was then poured into a mixture of water, ice and hydrochloric acid. The mixture was extracted with ether and the organic phase was evaporated to dryness under reduced pressure. The residue was chromatographed over silica gel and was eluted with a 8-1 cyclohexane-ethyl acetate mixture to obtain 4.56 g of (S) allethrolone 2,2-dimethyl-3R-(1',2',2',2'-tetrachloroethyl)-cyclopropane-1R-carboxylate with a melting point of 85° C.

Analysis: $C_{17}H_{20}Cl_4O_3$; molecular weight=414.16 Calculated: %C: 49.3; %H: 4.8; %Cl: 34.2; Found: %C: 49.0; %H: 4.8; %Cl: 35.5.

I.R. Spectrum (chloroform)

Absorptions at 1710 and 1730 cm$^{-1}$ (carbonyl), at 1655 and 1538 cm$^{-1}$ (C=C) and at 918 and 992 cm$^{-1}$ (—C=CH$_2$).

U.V. Spectrum (ethanol)

Max. at 227-228 nm $E_1^1$=357
Max. at 278 nm $E_1^1$=8

RMN Spectrum (deuterochloroform)

peaks at 1.32-1.37 ppm (hydrogens of geminal methyls); at 2.08 ppm (hydrogens of 2-methyl of allethrolone); at 2.98-3.08 ppm (hydrogens of methylene of allyl of allethrolone); at 4.12-4.23 and 4.28-4.39 ppm (1'-hydrogen of 3-ethyl of cyclopropane); at 4.83-5.25 ppm (terminal methylene of allyl of allethrolone); and at 5.5 to 6.17 ppm (hydrogen attached to 1'-carbon of allethrolone and hydrogen of carbon β to allyl chain of allethrolone).

EXAMPLE 24

3-phenoxy-benzyl 2,2-dimethyl-3S-(1',2'-dibromo-2',2'-dichloroethyl)-cyclopropane-1R-carboxylate 4 ml of pyridine were progressively added at 0° C. to a solution of 4.65 g of 2,2-dimethyl-3S-(1',2'-dibromo-2',2'-dichloroethyl)-cyclopropane-1R-carboxylic acid chloride and 2.40 g of 3-phenoxy-benzyl alcohol in 20 ml of benzene and the mixture was stirred for 17 hours and was then poured into aqueous hydrochloric acid. The mixture was extracted with benzene and the organic phase was washed with a saturated aqueous sodium bicarbonate solution, with water, dried over magnesium sulfate and evaporated to dryness under reduced pressure. The residue was chromatographed over silica gel and was eluted with a 9-1 petroleum ether (b.p.=35°-75° C.)-ethyl ether mixture to obtain 2.37 g of a mixture of the A and B isomers of 3-phenoxy-benzyl 2,2-dimethyl-3S-(1',2'-dibromo-2',2'-dichloroethyl)-cyclopropane-1R-carboxylate melting at 75° C.

Analysis: $C_{21}H_{20}Br_2Cl_2O_3$; molecular weight=551.11 Calculated: %C: 45.76; %H: 3.65; %Br: 29.0; %Cl: 12.86; Found: %C: 45.8; %H: 3.6; %Br: 28.5; %Cl: 12.9.

I.R. Spectrum (chloroform)

Absorption at 1725 cm$^{-1}$ (carbonyl) and at 1615, 1590 and 1492 cm$^{-1}$ (aromatic ring).

RMN Spectrum (deuterochloroform)

peaks at 1.25-1.37 and 1.22-1.39 ppm (hydrogens of geminal methyls); at 1.75-2.17 ppm (1- and 3-hydrogens of cyclopropane); at 5.1-5.16 ppm (hydrogens of methylene of benzyl); at 5.0-5.42 nd 5.35-5.53 ppm (1'-hydrogen of 3-ethyl of cyclopropane); and at 6.83-7.59 ppm (hydrogens of aromatic ring) RMN spectrum showed the product to be about ⅓ of isomer B and about ⅔ of isomer A. The starting acid chloride, described in example 15 may also be prepared as in example 16 starting with the 2,2-dimethyl 3R-(2',2'-dichlorovinyl)-cyclopropane-1R-carboxylic acid.

EXAMPLE 25

(S) allethrolone 2,2-dimethyl-3S-(1',2'-dibromo-2',2'-dichloroethyl)-cyclopropane-1R-carboxylate A mixture of 2 ml of pyridine and 2 ml of benzene were added at 0° C. to a solution of 1.75 g of (S) allethrolone and 4 g of 2,2-dimethyl-3S-(1',2'-dibromo-2',2'-dichloroethyl)-cyclopropane-1R-carboxylic acid chloride prepared from 3.6 g of the corresponding acid by the process of Step B of Example 24 in 40 ml of benzene and the mixture was stirred for 24 hours at 20° C. and was poured into a mixture of water-ice-hydrochloric acid. The mixture was extracted with benzene and the organic phase was washed with an aqueous saturated sodium bicarbonate solution and with water, dried over sodium sulfate and evaporated to dryness under reduced pressure to obtain 5.1 g of residue which was chromatographed over silica gel. Elution with a 97-3 benzene-ethyl acetate mixture yielded 4.25 g of (S) allethrolone 2,2-dimethyl-3S-(1',2'-dibromo-2',2'-dichloroethyl)-cyclopropane-1R-carboxylate.

Analysis: $C_{17}H_{20}Br_2Cl_2O_3$; molecular weight=503.07 Calculated: %C: 40.58; %H: 4.0; %Br: 31.76; %Cl: 14.09; Found: %C: 41.3; %H: 4.1; %Br: 31.0; %Cl: 14.2.

I.R. Spectrum (chloroform)

Absorption at 1718 cm$^{-1}$ (carbonyl), at 1655 and 1638 cm$^{-1}$ (C=C) and at 918-997 cm$^{-1}$ (—CH=CH$_2$).

RMN Spectrum (deuterochloroform)

peaks at 1.25-1.28 and 1.39-1.42 ppm (hydrogens of geminal methyls); at 1.95-2.07 ppm (hydrogens of 3'-methyl of allethrolone); at 4.83-6.17 ppm (hydrogens of terminal methylene of allyl of allethrolone); at 4.83-6.17 ppm (1'-hydrogen of 3-ethyl of cyclopropane); and at 5.75 ppm (4'-hydrogen of allethrolone).

EXAMPLE 26

5-benzyl-3-furyl-methyl 2,2-dimethyl-3S-(1',2'-dibromo-2',2'-dichloroethyl)-cyclopropane-1R-carboxylate A solution of 2.9 g of 5-benzyl-3-furyl-methyl alcohol in 15 ml of benzene was added at 0° C. to 12 ml of a 27 ml solution of 2,2-dimethyl-3S-(1',2'-dibromo-2',2'-dichloroethyl)-cyclopropane-1R-carboxylic acid chloride prepared from 10 g of the corresponding acid in benzene and then 3 ml of pyridine were added thereto. The mixture was stirred for 48 hours at 20° C. and was then poured into a water-ice-hydrochloric acid mixture. The mixture was extracted with benzene and the benzene extract was treated as before and evaporated to dryness. The residue was chromatographed over silica gel and was eluted with a 95-5 petroleum ether (b.p.=35°-75° C.)-ether mixture and then a 9-1 petroleum ether (b.p.=35°-75° C.)-ether mixture to obtain 2.2 g of 5-benzyl-3-furylmethyl 2,2-dimethyl-3S-(1',2'-dibromo-2',2'-dichloroethyl)cyclopropane-1R-carboxylate with a specific rotation $[\alpha]_D^{20} = -57.5°$ (c=0.4% in benzene).

Analysis: $C_{20}H_{20}Br_2Cl_2O_3$; molecular weight=539.104. Calculated: %C: 44.56; %H: 3.74; %Br: 29.04; %Cl: 13.15; Found: %C: 44.9; %H: 3.8; %Br: 29.1; %Cl: 13.3.

U.V. Spectrum (ethanol)

Inflex. at 252 nm $E_1^1 = 20$
Inflex. at 258 nm $E_1^1 = 15$
Inflex. at 264 nm $E_1^1 = 11$
Inflex. at 268 nm $E_1^1 = 9$

I.R. Spectrum (chloroform)

Absorption at 1720 cm$^{-1}$ (carbonyl) and at 1600, 1522 and 1493 cm$^{-1}$ (aromatic ring).

RMN Spectrum (deuterochloroform)

peaks at 1.23-1.35 and 1.20-1.38 ppm (hydrogens of 2-methyls of cyclopropane); at 1.67-2.17 ppm (1- and 3-hydrogens of cyclopropane); at 3.93 ppm (hydrogens of methylene of benzyl); at 4.93-5.0 ppm (hydrogens of carbon attached to carboxyl); at 6.02-6.1 ppm (3-hydrogen of furan); at 4.83-5.16-5.33-5.58 ppm (1'-hydrogen of 3-ethyl of cyclopropane); at 7.3 ppm (hydrogens of phenyl); and at 7.37 ppm (5-hydrogen of furan).

EXAMPLE 27

3,4,5,6-tetrahydrophthalimidomethyl 2,2-dimethyl-3S-(1',2'-dibromo-2',2'-dichloroethyl)-cyclopropane-1R-carboxylate The acid chloride prepared from 10 g of 2,2-dimethyl-3S-(1',2'-dibromo-2',2'-dichloroethyl)-cyclopropane-1R-carboxylic acid by the method of Example 24 was dissolved in benzene to obtain a total volume of 27 ml and 7.5 ml of the said solution were added to a solution of 1.4 g of 3,4,5,6-tetrahydrophthalimidomethyl alcohol in 15 ml of benzene. 2 ml of pyridine were added thereto at 0° C. and the mixture was stirred for 36 hours at 20° C. and was poured into a mixture of ice, water and hydrochloric acid. The mixture was extracted with benzene and the organic phase was washed with an aqueous saturated sodium bicarbonate solution, then with water, dried over sodium sulfate and evaporated to dryness under reduced pressure. The residue was chromatographed over silica gel and was eluted with a 9-1 benzene-ethyl acetate mixture to obtain 1.89 g of 3,4,5,6-tetrahydrophthalimidomethyl 2,2-dimethyl-3S-(1',2'-dibromo-2',2'-dichloroethyl)-cyclopropane-1R-carboxylate with a specific rotation of $[\alpha]_D^{20} = -53.5°$ (c=0.98% in benzene).

Analysis: $C_{17}H_{19}Br_2Cl_2NO_4$; molecular weight=532.07 Calculated: %C: 38.37; %H: 3.6; %Br: 30.03; %Cl: 13.32; %N: 2.63; Found: %C: 39.0; %H: 3.6; %Br: 28.3; %Cl: 12.7; %N: 2.6.

I.R. Spectrum (chloroform)

Absorptions at 1778, 1735 and 1723 cm$^{-1}$ (carbonyl) and at 1665 cm$^{-1}$ (—C═C—).

RMN Spectrum (deuterochloroform)

peaks at 1.21-1.22-1.39 ppm (hydrogens of geminal methyls); at 1.67-1.83 ppm (1- and 3-hydrogens of cyclopropane and methylenes α to —C═C—); at 2.37 ppm (methylenes α to —C═C—); at 5.0-5.5 ppm (1'-hydrogen of 3-ethyl of cyclopropane); and at 5.5-5.75 ppm (hydrogens of methylene α to carboxyl).

EXAMPLE 28

(R,S)α-cyano-3-phenoxy-benzyl dl cis-trans 2,2-dimethyl-3-(1',2'-dibromo-2',2'-dichloroethyl)-cyclopropane-1-carboxylate The starting (R,S)α-cyano-3-phenoxy-benzyl dl-cis trans 2,2-dimethyl-3-(2',2'-dichlorovinyl)-cyclopropane-1-carboxylate had the following characteristics:

U.V. Spectrum (ethanol)

Inflex. at 226 nm $E_1^1 = 522$
Inflex. at 267 nm $E_1^1 = 43$
Inflex. at 272 nm $E_1^1 = 47$
Max. at 278 nm $E_1^1 = 52$

RMN Spectrum (deuterochloroform)

peaks at 1.20-1.30 ppm (hydrogens of methyl groups); at 5.60-5.75 ppm (1'-hydrogen of dichlorovinyl of trans isomer); at 6.20-6.31 ppm (1'-hydrogen of dichlorovinyl of cis isomer); at 6.41-6.46 ppm (hydrogen on carbon α to —CN); and at 7.0 to 7.66 ppm (hydrogens of aromatic ring).

A solution of 0.85 ml of bromine in 10 ml of carbon tetrachloride were added over an hour to a solution of 6.7 g of the above indicated ester in 30 ml of carbon tetrachloride and the solution was stirred for 2 hours at 20° C. and was concentrated to dryness under reduced pressure. The 10 g of residue was chromatographed over silica gel and was eluted with a 9-1 cyclohexane-ethyl acetate mixture to obtain 7.5 g of (R,S)α-cyano-3-phenoxy-benzyl dl-cis trans 2,2-dimethyl-3-(1',2'-dibromo-2',2'-dichloroethyl)-cyclopropane-1-carboxylate.

Analysis: $C_{22}H_{19}Br_2Cl_2NO_3$; Calculated: %C: 45.86; %H: 3.32; %N: 2.43; %Cl 12.30; %Br: 27.74; Found: %C: 46.2; %H: 3.6; %N: 2.4; %Cl: 12.5; %Br: 27.5.

U.V. Spectrum (ethanol)

Inflex. at 267 nm $E_1^1 = 34$
Inflex. at 272 nm $E_1^1 = 35$
Max. at 277 nm $E_1^1 = 38$

RMN Spectrum (deuterochloroform)

peaks at 1.20-1.44 ppm (hydrogens of methyls); at 1.54-2.40 ppm (1- and 3-hydrogens of cyclopropane); at 4.21-4.51 ppm (1'-hydrogen of dichlorovinyl of trans isomer); at 4.97 to 5.40 ppm (1'-hydrogen of dichlorovinyl of cis isomer); at 6.42 to 6.50 ppm (hydrogen on carbon α to —CN); and at 7.0 to 7.55 ppm (hydrogens of aromatic ring).

EXAMPLE 29

5-benzyl-3-furyl-methyl 2,2-dimethyl-3R-(1',2'-dibromo-2',2'-dichloroethyl)-cyclopropane-1R-carboxylate 5 ml of pyridine were added dropwise to a mixture of 30 ml of benzene, 3.2 g of 5-benzyl-3-furyl-methanol and 7.6 g of 2,2-dimethyl-3R-(1',2'-dibromo-2',2'-dichloroethyl)-cyclopropane-1R-carboxylic acid chloride [prepared from the acid of Example 10 by the procedure of Example 16] and the mixture was stirred for 48 hours at 20° C. Water was added thereto and the organic phase was decanted. The aqueous phase was extracted with benzene and the combined organic phases were dried and evaporated to dryness under reduced pressure. The residue was chromatographed over silica gel and was eluted with a 7-3 benzene-cyclohexane mixture to obtain 6.1 g of 5-benzyl-3-furyl-methyl 2,2-dimethyl-3R-(1',2'-dibromo-2',2'-dichloroethyl)-cyclopropane-1R-carboxylate with a specific rotation of $[\alpha]_D^{20} = -19°$ (c=0.5% in benzene).

Analysis: $C_{20}H_{20}Br_2Cl_2O_3$; molecular weight=539.09 Calculated: %C: 44.56; %H: 3.74; %Br: 29.65; %Cl: 13.15; Found: %C: 44.2; %H: 3.7; %Br: 29.4; %Cl: 13.5.

I.R. Spectrum

Absorption at 1725 cm$^{-1}$ (carbonyl) and at 1555, 1540, 1498 and 1495 cm$^{-1}$ (—C=C— and aromatic ring).

U.V. Spectrum (ethanol)

Inflex. at 216 nm $E_1^1 = 265$
Inflex. at 251 nm $E_1^1 = 10.5$
Max. at 257 nm $E_1^1 = 8.5$
Inflex. at 261 nm $E_1^1 = 7$
Inflex. at 263 nm $E_1^1 = 6$
Max. at 268 nm $E_1^1 = 4.5$

RMN Spectrum (deuterochloroform)

peaks at 1.22-1.25-1.28 ppm (hydrogens of geminal methyls); at 1.6-2.32 ppm (1- and 3-hydrogens of cyclopropane); 3.93 ppm (hydrogens of methylene of benzyl); at 4.25-4.37-4.54 ppm (1'-hydrogen of 3-ethyl of cyclopropane); 4.95-4.97 ppm and 6.0-6.05 ppm (hydrogens of methylene α to carboxyl); at 7.33 ppm (4-hydrogen of furyl); and at 7.25 ppm (hydrogens of phenyl).

EXAMPLE 30

3-phenoxy-benzyl 2,2-dimethyl-3R-(1',2'-dibromo-2',2'-dichloroethyl)-cyclopropane-1R-carboxylate A solution of 19.35 g of 2,2-dimethyl-3R-(1',2'-dibromo-2',2'-dichloroethyl)-cyclopropane-1R-carboxylic acid chloride in benzene was added dropwise to a solution of 9 g of 3-phenoxy-benzyl alcohol, 50 ml of benzene and 10 ml of pyridine and the mixture was stirred at 20° C. for 18 hours and was then poured into water. The mixture was extracted with benzene and the organic phase was dried over magnesium sulfate and was evaporated to dryness. The residue was chromatographed over silica gel and was eluted with a 95-5 petroleum ether (b.p.=35°-75° C.)-ethyl ether mixture to obtain 8.1 g of 3-phenoxy-benzyl 2,2-dimethyl-3R-(1',2'-dibromo-2',2'-dichloroethyl)-cyclopropane-1R-carboxylate with a specific rotation of $[\alpha]_D^{20} = -20.5°$ (c=0.6% in benzene).

Analysis: $C_{21}H_{20}Br_2Cl_2O_3$; molecular weight=551.11 Calculated: %C: 45.17; %H: 3.66; %Br 29.0; %Cl 12.87; Found: %C: 45.7; %H: 3.7; %Br 28.5; %Cl 13.0.

I.R. Spectrum (chloroform)

Absorption at 1730 cm$^{-1}$ (carbonyl) and at 1618 and 1590 cm$^{-1}$ (aromatic ring).

U.V. Spectrum (ethanol)

Inflex. at 228 nm $E_1^1 = 216$
Inflex. at 267 nm $E_1^1 = 34$
Max. at 272 nm $E_1^1 = 37.5$
Max. at 278 nm $E_1^1 = 36$

RMN Spectrum (deuterochloroform)

peaks at 1.22-1.27-1.29 ppm (hydrogens of geminal methyls); at 1.66-1.75 ppm and 1.92-2.13 ppm (1-hydrogen of cyclopropane); at 1.92-2.33 ppm (3-hydrogen of cyclopropane); at 4.22-4.38 and 4.38-4.57 ppm (1'-hydrogen of 3-ethyl of cyclopropane); at 5.12-5.13 ppm (hydrogens of methylene of benzyl); and at 6.83-7.53 ppm (hydrogens of aromatic ring).

EXAMPLE 31

3,4,5,6-tetrahydrophthalimidomethyl 2-dimethyl-3R-(1',2'-dibromo-2',2'-dichloroethyl)-cyclopropane-1R-carboxylate 2.5 ml of pyridine were added dropwise to a solution of 0.930 g of 3,4,5,6-tetrahyrophthalimidomethyl alcohol and 2 g of 2,2-dimethyl-3R-(1',2'-dibromo-2',2'-dichloroethyl)-cyclopropane-1R-carboxylic acid chloride in 20 ml of benzene and the mixture was stirred for 48 hours at 20° C. Water was added thereto and the mixture was extracted with benzene. The combined organic phases were evaporated to dryness and the residue was chromatographed over silica gel. Elution with a 9-1 benzene-ethyl acetate mixture yielded 2.17 g of 3,4,5,6-tetrahydrophthalimidomethyl 2,2-dimethyl-3R-(1',2'-dibromo-2',2'-dichloroethyl)-cyclopropane-1R-carboxylate melting at 117° C. and having a specific rotation of $[\alpha]_D^{20} = -6.5°$ (c=0.9% in benzene).

Analysis: $C_{17}H_{19}Br_2Cl_2NO_4$; molecular weight=532.066 Calculated: %C: 38.38; %H 3.60; %Br 30.04; %Cl 13.32; %N 2.63; Found: %C: 38.5; %H 3.5; %Br 29.9; %Cl 13.4; %N 2.5.

I.R. Spectrum (chloroform)

Absorption at 1783 cm$^{-}$(carbonyl); at 1728 and 1750 cm$^{-1}$ (carbonyl and ester functions); and at 1669 cm$^{-1}$ (carbonyl).

U.V. Spectrum (ethanol)

Max. at 223 nm $E_1^1 = 301$
Max. at 229-230 nm $E_1^1 = 293$
Inflex. at 236 nm $E_1^1 = 172$
Inflex. at 272 nm $E_1^1 = 8$

EXAMPLE 32

3-phenoxy-benzyl
2,2-dimethyl-3R-(1',2'-dichloro-2',2'-dibromoethyl)-cyclopropane-1R-carboxylate STEP A:
2,2-dimethyl-3R-(1',2'-dichloro-2',2'-dibromoethyl)cyclopropane-1R-carboxylic acid 24 g of 2,2-dimethyl-3S-(2',2'-dibromovinyl)-cyclopropane-1R-carboxylic acid were added to a mixture of 20 ml of carbon tetrachloride and 20 ml of methylene chloride and chlorine was bubbled into the reaction mixture at −10° C. provided in the reaction area with a refrigerant with methanol circulating at −60° C. The mixture was stirred for 2½ hours at −10° C. and for 90 minutes at +10° C. and excess chlorine was allowed to evaporate. The mixture was evaporated to dryness under reduced pressure and the residue was chromatographed over silica gel. Elution with a 75-25-1 cyclohexane-ethyl acetate-acetic acid mixture yielded 16.3 g of 2,2-dimethyl-3R-(1',2'-dichloro-2',2'-dibromoethyl)-cyclopropane-1R-carboxylic acid.

RMN Spectrum (deuterochloroform)

peaks at 1.33–1.56 ppm (hydrogens of geminal methyls); at 1.7–12.25 ppm (1- and 3-hydrogens of cyclopropane); at 4.11–4.37 ppm (1'-hydrogen of 3-methyl of cyclopropane); and at 10.8 ppm (carboxyl hydrogen).

STEP B: 3-phenoxy-benzyl
2,2-dimethyl-3R-(1',2'-dichloro-2',2'-dibromoethyl)-cyclopropane-1R-carboxylate A solution of the acid chloride obtained from 4.5 g of 2,2-dimethyl-3R-(1',2'-dichloro-2',2'-dichloroethyl)cyclopropane-1R-carboxylic acid prepared by Step B of Example 16 in 7 ml of benzene was added at 0° C. to a solution of 2.7 g of 3-phenoxy-benzyl alcohol in 7 ml of benzene and 1.5 ml of pyridine was added thereto. The mixture was stirred for 16 hours at 20° C. and was poured into a mixture of water, ice and hydrochloric acid. The mixture was extracted with ether and the organic phase was washed with water, dried over magnesium sulfate and evaporated to dryness under reduced pressure. The 6.37 g of residue was chromatographed over silica gel and eluted with a 9-1 cyclohexane-ethyl acetate mixture to obtain 2.09 g of 3-phenoxy-benzyl 2,2-dimethyl-3R-(1',2'-dichloro-2',2'-dibromoethyl)-cyclopropane-1R-carboxylate.

Analysis: $C_{21}H_{20}Cl_2Br_2O_3$; molecular weight = 551.12 Calculated: %C: 45.7; %H 3.6; %Br 29; %Cl 12.8; Found: %C: 46.0; %H 3.8; %Br 29.4. 12.6;

I.R. Spectrum (chloroform)

Absorption at 1730 cm$^{-1}$ (carbonyl) and at 1615, 1590 cm$^{-1}$ (aromatic ring).

U.V. Spectrum (ethanol)

Inflex. at 220 nm $E_1^1 = 205$
Inflex. at 266 nm $E_1^1 = 33$
Max. at 271–272 nm $E_1^1 = 36$
Max. at 278 nm $E_1^1 = 34$ RMN Spectrum (deuterochloroform)

peaks at 1.25–1.28–1.33 ppm (hydrogens of geminal methyls); at 1.72–2.42 ppm (1- and 3-hydrogens of cyclopropane); at 3.98–4.35 ppm (1'-hydrogen of 3-ethyl of cyclopropane); 6.85–7.5 ppm (hydrogens of aromatic ring); and at 5.13 ppm (hydrogens of methylene of benzyl).

EXAMPLE 33

(S) allethrolone
2,2-dimethyl-3R-(1',2'-dichloro-2',2'-dibromoethyl)-cyclopropane-1R-carboxylate A solution of the acid chloride formed from 4.5 g of 2,2-dimethyl-3R-(1',2'-dichloro-2',2'-dibromoethyl)-cyclopropane-1R-carboxylic acid in 7 ml of benzene was added at 0° C. to a solution of 2.05 g of (S) allethrolone in 7 ml of benzene and 1.5 ml of pyridine were added thereto. The mixture was stirred for 16 hours at 20° C. and was poured into a mixture of water, ice and hydrochloric acid. The mixture was extracted with ether and the organic phase was washed with water, dried over magnesium sulfate and evaporated to dryness. The 5.15 g of residue was chromatographed over silica gel and was eluted with a 4-1 cyclohexane-ethyl acetate mixture to obtain 1.86 g of (S) allethrolone 2,2-dimethyl-3R-(1',2'-dichloro-2',2'-dibromoethyl)-cyclopropane-1R-carboxylate melting at 126° C.

I.R. Spectrum (chloroform)

Absorption at 1713 and 1730 cm$^{-1}$ (carbonyl); at 1658 and 1642 cm$^{-1}$ (—C=C—) and at 923 and 995 cm$^{-1}$ (—CH=CH$_2$).

U.V. Spectrum (ethanol)

Max. at 229 nm $E_1^1 = 315$
Inflex. at 300 nm $E_1^1 = 1$

RMN Spectrum (deuterochloroform)

peaks at 1.32–1.35–1.38 ppm (hydrogens of geminal methyls); at 4.23–4.4 and 4.1–4.27 ppm (1'-hydrogen of 3-ethyl of cyclopropane); at 2.08–2.15 ppm (hydrogens of 3-methyl of allethrolone); at 2.98–3.08 ppm (5-methylene of allethrolone); at 4.85–5.25 ppm (hydrogens of terminal methylene of allethrolene); at 5.5–6.17 ppm (hydrogen β to allyl of allethrolone); and at 5.83 (4'-hydrogen of allethrolone).

EXAMPLE 34

3-phenoxy-benzyl
2,2-dimethyl-3S-(1',2'-dichloro-2',2'-dibromoethyl)-cyclopropane-1R-carboxylate STEP A:
2,2-dimethyl-3S-(1',2'-dichloro-2',2'-dibromoethyl)cyclopropane-1R-carboxylic acid chloride A mixture of 5 g of 2,2-dimethyl-3S-(1',2'-dichloro-2',2'-dibromoethyl)-cyclopropane-1R-carboxylic acid, 10 ml of thionyl chloride and 30 ml of petroleum ether (b.p. = 35°–70° C.) was refluxed for 4 hours and was evaporated to dryness under reduced pressure. The residue was added to benzene and the solution was evaporated to dryness under reduced pressure to obtain 5.4 g of 2,2-dimethyl-3S-(1',2'-dichloro-2',2'-dibromoethyl)-cyclopropane-1R-carboxylic acid chloride.

STEP B: 3-phenoxy-benzyl
2,2-dimethyl-3S-(1',2'-dichloro-2',2'-dibromoethyl)-cyclopropane-1R-carboxylate A solution of 4.35 g of pyridine in 10 ml of benzene was progressively added at 8° C. to a mixture of 5.4 g of the acid chloride of Step A, 3.2 g of 3-phenoxy-benzyl alcohol and 38 ml of benzene and the mixture was stirred at 20° C. for 17 hours and was then poured into a mixture of ice and water. The mixture was extracted with benzene and the organic phase was dried over magnesium sulfate and was evaporated to dryness. The residue was chromatographed over silica gel and was eluted with a 7-3 benzene-ethyl acetate mixture to obtain a product which was crystallized from petroleum ether (b.p.=35°–70° C.) to obtain 4.7 g of 3-phenoxybenzyl 2,2-dimethyl-3S-(1',2'-dichloro-2',2'-dibromoethyl)cyclopropane-1R-carboxylate melting at 68° C. and having a specific rotation of $[\alpha]_D^{20} = -34°$ (c=1% chloroform).

Analysis: $C_{21}H_{20}Cl_2Br_2O_3$; molecular weight=551.20 Calculated: %C 45.76 %H: 3.66; %Br: 29.00; %Cl: 12.86; Found: %C: 46.0 %H: 3.6; %Br 29.3; %Cl: 12.7.

I.R. Spectrum (chloroform)

Absorption at 1725 cm$^{-1}$ (carbonyl) and at 1615, 1588 and 1490 cm$^{-1}$ (aromatic ring).

U.V. Spectrum (ethanol)

Inflex. at 227 nm $E_1^1 = 214$
Inflex. at 266 nm $E_1^1 = 33$
Max. at 272 nm $E_1^1 = 35$
Max. at 278 nm $E_1^1 = 36$ RMN Spectrum (deuterochloroform)

peaks at 1.22–1.39 ppm and 1.26–1.42 ppm (hydrogens of geminalmethyls) at 1.66–2.08 ppm (1- and 3-hydrogens of cyclopropane); at 4.8–5.37 ppm (hydrogens of

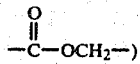

and at 6.83–7.58 ppm (hydrogens of aromatic ring).

EXAMPLE 35

(S) allethrolone 2,2-dimethyl-3S-(1',2'-dibromo-2',2'-difluoroethyl)-cyclopropane-1R-carboxylate STEP A:
2,2-dimethyl-3S-(1',2'-dibromo-2',2'-difluoroethyl)cyclopropane-1R-carboxylic acid A solution of 15.2 g of bromine in 40 ml of carbon tetrachloride was added over 2 hours at −65° C. to a solution of 17 g of 2,2-dimethyl-3R-(2',2'-difluorovinyl)-cyclopropane-1R-carboxylic acid in 120 ml of methylene chloride and the mixture was stirred for 2½ hours at −65° C. after which the temperature was allowed to return to room temperature. The mixture was evaporated to dryness under reduced pressure and the residue was dissolved in 50 ml of hot carbon tetrachloride. The solution was cooled to 0° C. and was stirred at 0° C. for 45 minutes and was then filtered. The filtrate was evaporated to dryness under reduced pressure and the residue was dissolved in 40 ml of carbon tetrachloride. The mixture was stirred at −10° C. for 30 minutes and was filtered. The filtrate was evaporated to dryness under reduced pressure and the residue was chromatographed over silica gel. Elution with a 3-1 cyclohexane-ethyl acetate mixture yielded a product which was crystallized from petroleum ether (b.p.=35°–75° C.) to obtain 1.465 g of 2,2-dimethyl-3S-(1',2'-dibromo-2',2'-difluoroethyl)-cyclopropane-1R-carboxylic acid melting at 124° C.

RMN Spectrum (deuterochloroform)

peaks at 1.28–1.38 ppm (hydrogens of geminal methyls); at 1.67–2.0 ppm (1- and 3-hydrogens of cyclopropane); and at 4.67–5.33 ppm (1'-hydrogen of 3-ethyl of cyclopropane).

STEP B:
2,2-dimethyl-3S-(1',2'-dibromo-2',2'-difluoroethyl)cyclopropane-1R-carboxylic acid chloride A mixture of 2.5 ml of thionyl chloride, 1.43 g of the acid of Step A and 15 ml of petroleum ether (b.p.=35°–75° C.) was refluxed for 4½ hours and then excess thionyl chloride was removed and the mixture was evaporated to dryness under reduced pressure. The residue was taken up in benzene and the solution was evaporated to dryness under reduced pressure to obtain 2,2-dimethyl-3S-(1',2'-dibromo-2',2'-difluoroethyl)-cyclopropane-1R-carboxylic acid chloride which was used as is for the next step.

STEP C: (S) allethrolone 2,2-dimethyl-3S-(1',2'-dibromo-2',2'-difluoroethyl)-cyclopropane-1R-carboxylate A solution of 0.7 g of (S) allethrolone in 5 ml of benzene was added at 2° C. to a solution of the product of Step B in 10 ml of benzene and after the addition of 0.5 ml of pyridine, the mixture was stirred for 16 hours at 20° C. The mixture was poured into a water-ice-hydrochloric acid mixture and the mixture was extracted with ethyl ether. The organic phase was washed with water, dried over sodium sulfate and evaporated to dryness to obtain 2.02 g of raw product. The latter was chromatographed over silica gel and was eluted with a 4-1 cyclohexane-ethyl acetate mixture to obtain 1.224 g of (S) allethrolone 2,2-dimethyl-3S-(1',2'-dibromo-2',2'-difluoroethyl)-cyclopropane-1R-carboxylate.

Analysis: $C_{17}H_{20}Br_2F_2O_3$; molecular weight=470.162 Calculated: %C: 43.4; %H: 4.3; %Br: 34.0; %F 8.1; Found: %C: 43.2; %H: 4.4; %Br: 33.7; %F: 8.1.

U.V. Spectrum (ethanol)

Max. at 227–228 nm $E_1^1 = 348$

RMN Spectrum (deuterochloroform)

peaks at 1.25–1.36 ppm (hydrogens of geminal methyls); at 2.02–2.06 ppm (hydrogens of 2-methyl of allethrolone); at 4.83–5.25 ppm (hydrogens of terminal methylene of allyl of allethrolone); at 5.5–6.17 ppm (hydrogen β to lateral chain of allethrolone and hydrogen of 1-carbon of allethrolone); at 4.83–6.17 ppm (1'-hydrogen of 3-ethyl of cyclopropane); at 1.67–2.16 ppm (1- and 3-hydrogens of cyclopropane); at 2.95–3.05 ppm (hydrogens of methylene α- to side chain of allethrolone); and at 1.67–3.17 ppm (methylene of allethrolone ring).

EXAMPLE 36

(R,S)α-cyano-3-phenoxy-benzyl 2,2-dimethyl-3S-(1',2'-dibromo-2',2'-difluoroethyl)cyclopropane-1R-carboxylate

STEP A:
2,2-dimethyl-3S-(1',2'-dibromo-2',2'-difluoroethyl)cyclopropane-1R-carboxylic acid chloride A mixture of 7 ml of thionyl chloride, 2.5 g of 2,2-dimethyl-3S-(1',2'-dibromo-2',2'-difluoroethyl)-cyclopropane-1R-carboxylic acid and 15 ml of petroleum ether (b.p.=35°-75° C.) was refluxed for 13½ hours and was evaporated to dryness under reduced pressure. The residue was taken up in benzene and the solution was evaporated to dryness to obtain 2,2-dimethyl-3S-(1',2'-dibromo-2',2'-difluoroethyl)-cyclopropane-1R-carboxylic acid chloride which was used as is for the next step.

STEP B: (R,S)α-cyano-3-phenoxy-benzyl 2,2-dimethyl-3S-(1',2'-dibromo-2',2'-difluoroethyl)-cyclopropane-1R-carboxylate A solution of 1.995 g of (R,S)α-cyano-3-phenoxybenzyl alcohol in 10 ml of benzene was added at 2° C. to a solution of the product of Step A in 15 ml of benzene and after the addition of 1 ml of pyridine, the mixture was stirred for 16 hours at 20° C. and was poured into a water-ice-hydrochloric acid mixture. The mixture was extracted with ether and the organic phase was evaporated to dryness. The residue was chromatographed over silica gel and was eluted with a 9-1 cyclohexane-ethyl acetate mixture to obtain 1.972 g of (R,S) α-cyano-3-phenoxy-benzyl 2,2-dimethyl-3S-(1',2'-dibromo-2',2'-difluoroethyl)-cyclopropane-1R-carboxylate.

Analysis: $C_{22}H_{19}Br_2F_2NO_3$; molecular weight=543.22 Calculated: %C: 48.6; %H 3.5; %Br 29.4; %F: 7.0; %N; 2.6; Found: %C: 48.9; %H 3.5; %Br 29.6; %F: 7.1; %N: 2.5.

I.R. Spectrum (chloroform)

Absorption at 1735 cm$^{-1}$ (carbonyl) and at 1588, 1610 and 1487 cm$^{-1}$ (aromatic ring).

U.V. Spectrum (ethanol)

Inflex. at 230 nm $E_1^1=208$
Inflex. at 268 nm $E_1^1=34$
Inflex. at 273 nm $E_1^1=37$
Max. at 278 nm $E_1^1=40$
Inflex. at 285 nm $E_1^1=29$

RMN Spectrum (deuterochloroform)

peaks at 1.03-1.45 ppm (hydrogens of geminal methyls); at 1.75-2.0 ppm (1- and 3-hydrogens of cyclopropane); at 4.42-5.17 ppm (1'-hydrogen of 3-ethyl of cyclopropane); at 6.4-6.47 ppm (hydrogen α- to -CN); and at 6.92-7.67 ppm (hydrogens of aromatic ring).

EXAMPLE 37

3-phenoxy-benzyl 2,2-dimethyl-3R-(1',2'-dibromo-2',2'-difluoroethyl)-cyclopropane-1R-carboxylate

STEP A:
2,2-dimethyl-3R-(1',2'-dibromo-2',2'-difluoroethyl)cyclopropane-1R-carboxylic acid A solution of 24 g of bromine in 50 ml of carbon tetrachloride was added at −65° C. over 90 minutes to a solution of 26.4 g of 2,2-dimethyl-3S-(2',2'-difluorovinyl)-cyclopropane-1R-carboxylic acid in 150 ml of methylene chloride and the mixture was stirred at −60° C. for 3 hours and was then allowed to return to 20° C. The mixture was evaporated to dryness under reduced pressure and the residue was crystallized from petroleum ether to obtain 14.09 g of 2,2-dimethyl-3R-(1',2'-dibromo-2',2'-difluoroethyl)-cyclopropane-1R-carboxylic acid melting at 116° C.

Analysis: $C_8H_{10}Br_2F_2O_2$; molecular weight=335.98 Calculated: %C: 28.6; %H: 3.0; %BR: 47.6; %F: 11.3; Found: %C: 28.8; %H: 3.1; %Br: 47.7; %F: 11.5.

RMN Spectrum (deuterochloroform)

Peaks at 1.33 ppm (hydrogens of geminal methyls); at 1.5-2.33 ppm (1- and 3-hydrogens or cyclopropane); at 3.67-4.41 ppm (1'-hydrogen of 3-ethyl of cyclopropane); and at 10.9 ppm (carboxyl hydrogen).

STEP B:
2,2-dimethyl-3R-(1',2'-dibromo-2',2'-difluoroethyl)cyclopropane-1R-carboxylic acid chloride A mixture of 10 ml of thionyl chloride, 11 g of 2,2-dimethyl-3S-(1',2'-dibromo-2',2'-difluoroethyl)-cyclopropane-1R-carboxylic acid and 40 ml of petroleum ether (b.p.=35°-75° C.) was refluxed for 4 hours and after elimination of excess thionyl chloride, the mixture was evaporated to dryness under reduced pressure. The residue ws taken up in benzne and the solution was evaporated to dryness to obtain 2,2-dimethyl-3R-(1',2'-dibromo-2',2'-difluoroethyl)-cyclopropane-1R-carboxylic acid chloride which was used as is for the next step.

STEP C: 3-phenoxy-benzyl 2,2-dimethyl-3R-(1',2'-dibromo-2',2'-difluoroethyl)-cyclopropane-1R-carboxylate The product of Step B was dissolved in 50 ml of benzene to obtain a final solution of 56 ml and 18.5 ml thereof was added at 2° C. to a solution of 2.4 g of 3-phenoxybenzyl alcohol in 2.5 ml of benzene. 1 ml of pyridine was added thereto and the mixture was stirred at 20° C. for 16 hours. The reaction mixture was poured into a water-ice-hydrochloric acid mixture and the mixture was extracted with ether. The organic phase was washed with water, dried over magnesium sulfate and evaporated to dryness. The residue was chromatographed over silica gel and was eluted with a 95-5 cyclohexane-benzene mixture to obtain 3.204 g of 3-phenoxybenzyl 2,2-dimethyl-3R-(1',2'-dibromo-2',2'-difluoroethyl)cyclopropane-1R-carboxylate.

Analysis: $C_{21}H_{20}Br_2F_2O_3$; molecular weight=518.206 Calculated: %C: 48.7; %H: 3.9; %Br: 30.9; %F: 7.3; Found: %C: 48.9 %H: 3.9; %BR: 31.0: %F: 7.1.

U.V. Spectrum (ethanol)

Inflex. at 225 nm $E_1^1=225$
Inflex. at 265 nm $E_1^1=33$
Max. at 271 nm $E_1^1=37$
Max. at 277 nm $E_1^1=36$

RMN Spectrum (deuterochloroform):

Peaks at 1.27 (hydrogens of geminal methyls); at 1.58-2.17 ppm (1- and 3-hydrogens of cyclopropane); at 3.67-4.33 ppm (1'-hydrogen of 3-ethyl of cyclopropane); at 5.13 ppm (methylene α-to carboxyl); and at 7.58-7.75 ppm (hydrogens of aromatic ring).

EXAMPLE 38

(R,S,) α-cyano-3-phenoxy-benzyl 2,2-dimethyl-3R-(1',2'-dibromo-2',2'-difluoroethyl)-cyclopropane-1R-carboxylate 11 g of 2,2-dimethyl-3R-(1',2'-dibromo-2',2'-difluoroethyl)-cyclopropane-1R-carboxylic acid was used to prepare the acid chloride thereof which was dissolved in 50 ml of benzene and a solution of 5.4 ml of α-cyano-3-phenoxy-benzyl alcohol in 5 ml of benzene was added at 0° C. to 37.5 ml of the resulting solution. 2 ml of pyridine were added thereto and the mixture was stirred at 20° C. for 16 hours. The mixture was poured into a water-ice-hydrochloric acid mixture and the resulting mixture was extracted with ether. The organic phase was treated as before and evaporated to dryness under reduced pressure. The residue was chromatographed over silica gel and was eluted with a 9-1 cyclohexane-ethyl acetate mixture to obtain 5.46 g of (R,S)α-cyano-3-phenoxy-benzyl 2,2-dimethyl-3R-(1',2'-dibromo-2',2'-difluoroethyl)-cyclopropane-1R-carboxylate.

Analysis: $C_{22}H_{19}Br_2F_2O_3N$; molecular weight=543.22 Calculated: %C: 48.6; %H: 3.5; %Br: 29.4; %F: 7; %N: 2.6; Found: %C: 49.1; %H: 3.5; %Br: 28.8; %F: 6.7; %N: 2.5.

I.R. Spectrum (chloroform)

Absorption at 1745 cm$^{-1}$ (carbonyl); at 1615–1590 cm$^{-1}$ (of aromatic ring).

U.V. Spectrum (ethanol)

Inflex. at 230 nm $E_1^1$=192
Inflex. at 269 nm $E_1^1$=34
Inflex. at 273 nm $E_1^1$=36
Max. at 278 nm $E_1^1$=39
Inflex. at 305 nm $E_1^1$=1

RMN Spectrum (deuterochloroform)

Peaks at 1.2–1.33 ppm (hydrogens of geminal methyls); at 1.9–2.25 ppm (1- and 3-hydrogens of cyclopropane); at 3.66–4.33 ppm (1'-hydrogen of 3-ethyl of cyclopropane); at 6.45 ppm (hydrogen attached to same carbon as —CN); and at 6.91–7.58 ppm (hydrogens of aromatic ring).

EXAMPLE 39

A and B isomers of 3-phenoxy-benzyl 2,2-dimethyl-3S-(1',2'-dibromo-2'-chloro-2'(R,S)-fluoroethyl)-cyclopropane-1R-carboxylate

STEP A:

2,2-dimethyl-3S-(1',2'-dibromo-2'-chloro-2'-(R,S) fluoroethyl)-cyclopropane-1R-carboxylic acid A solution of 2.4 ml of bromine in 20 ml of carbon tetrachloride was added at −10° C. over 30 minutes to a solution of 8.9 g of a mixture of the E and Z isomers of 2,2-dimethyl-3R-(2'-chloro-2'-fluorovinyl)-cyclopropane-1R-carboxylic acid in 100 ml of carbon tetrachloride and the mixture was stirred at 10° C. for 4 hours. The mixture was evaporated to dryness under reduced pressure and the residue was chromatographed over silica gel. Elution with ethyl acetate yielded 13.7 g of 2,2-dimethyl-3S-(1',2'-dibromo-2'-(R,S)-fluoro-2'-chloroethyl)-cyclopropane-1R-carboxylic acid.

I.R. Spectrum (chloroform)

Absorption at 1710 cm$^{-1}$ (carbonyl) and 3510 cm$^{-1}$ (OH).

RMN (Spectrum (deuterochloroform)

Peaks at 1.30–1.32–1.42 ppm (hydrogens of geminal methyls); at 1.75–2.08 ppm (1- and 3-hydrogens of cyclopropane); at 4.67–5.50 ppm (1'-hydrogen of 3-ethyl of cyclopropane); and at 10.75 ppm (carboxyl hydrogen).

STEP B: phenoxy-benzyl 2,2-dimethyl-3S-(1',2'-dibromo-2'-(R,S)-fluoro-2'-chloroethyl)-cyclopropane-1R-carboxylate A mixture of 3.5 g of the acid of Step A, 3.5 g of 3-phenoxy-benzyl alcohol, 3.5 g of neopentyl acetal of dimethylformamide and 35 ml of benzene was heated for 17 hours at 50° C. and was then cooled and evaporated to dryness under reduced pressure. The residue was chromatographed over silica gel and was eluted with a 1-1 benzene-cyclohexane mixture to obtain 1.050 g of the A isomer of 3-phenoxy-benzyl 2,2-dimethyl-3S-(1',2'-dibromo-2'-(R,S)-fluoro-2'-chloroethyl)-cyclopropane-1R-carboxylate melting at 50° C.

Analysis: $C_{21}H_{20}Br_2ClFO_3$; molecular weight=534.65 Calculated: %C: 47.17; %H: 3.77; %BR: 29.89; %Cl: 6.63; %F: 3.55; Found: %C: 47.4; %H: 3.8; %Br: 29.4; %Cl: 7.2; %F: 3.7.

I.R. Spectrum (chloroform)

Absorption at 1735 cm$^{-1}$ (carbonyl) and 1675, 1590 and 1490 cm$^{-1}$ (aromatic ring).

RMN Spectrum (deuterochloroform)

Peaks at 1.23–1.39 ppm (hydrogens of geminal methyls); at 1.73–2.01 ppm (1- and 3-hydrogens of cyclopropane); at 5.08 ppm (hydrogens of methylene of benzyl); at 5.08–5.50 ppm (1'-hydrogen of 3-ethyl of cyclopropane); and at 6.83–7.58 ppm (hydrogens of aromatic ring).

Also recovered were 0.62 g of the B isomer of the same ester having the following charactertics:

Analysis:
Calculated: %C: 47.17; %H: 3.77; %Cl: 6.03; %F: 3.55; %Br: 29.89; Found: %C: 47.5; %H: 3.8; %Cl: 6.2; %F: 3.6; %Br: 29.6;

I.R. Spectrum (chloroform): identical to that of isomer A.

RMN Spectrum (deuterochloroform)

Peaks at 1.22–1.34 ppm (hydrogens of geminal methyls); at 1.75–2.0 ppm (1- and 3-hydrogens of cyclopropane); at 5.12 ppm (hydrogens of methylene of benzyl); at 4.83–5.33 ppm (1'-hydrogen of 3-ethyl of cyclopropane); and at 5.83–7.5 ppm (hydrogens of aromatic ring).

The starting acid was prepared by the procedure of Brown [thesis of 1974 entitled Structure Activity Studies of Halopyrethroids published in 1976 by Xerox University Microfilms, Ann Arbor., Michigan, p. 27 to 29] to make the corresponding dl-trans acid but using tert.-butyl 2,2-dimethyl-3S-formyl-cyclopropane-1R-carboxylate in place of tert.-butyl 2,2-dimethyl-3RS-formyl-cyclopropane-1RS-carboxylate.

EXAMPLE 40

3,4,5,6-tetrahydrophthalimidomethyl (1R, cis) 2,2-dimethyl-3-(1',2',2',2'-tetrabromoethyl)-cyclopropane-1-carboxylate

STEP A: (1R,cis) 2,2-dimethyl-3-(1',2',2',2'-tetrabromoethyl)-cyclopropane-1-carboxylic acid 19.4 g of (1R, cis) 2,2-dimethyl-3-(2',2'-dibromovinyl)-cyclopropane-1-carboxylic acid were added to 150 ml of carbon tetrachloric and then a solution of 10.4 g of bromine in 22 ml of carbon tetrachloride was added thereto. The mixture was stirred at 20° C. for one hour and was then concentrated to dryness under reduced pressure to obtain 31.4 g of raw product melting at 145° C. The latter was crystallized from 110 ml of carbon tetrachloride to obtain 22.12 g of (1R, cis) 2,2-dimethyl-3-(1',2',2',2'-tetrabromoethyl)-cyclopropane-1-carboxylic acid melting at 150° C. which was a mixture of (A) and (B) isomers as determined by the RMN Spectrum.

The RMN Spectrum detected a compound corresponding to about ⅔ of the mixture with peaks at 1.31 to 1.43 ppm (hydrogens of geminal methyls) and peaks at 5.33 to 5.66 ppm (hydrogen fixed to asymetrical monobromo carbon atom) and another compound corresponding to about ⅓ of the mixture with peaks at 1.28–1.48 ppm (hydrogens of geminal methyls) and peaks at 4.24 to 5.34 ppm (hydrogen fixed to asymetrical monobromo carbon atom). In the mixture, there were also peaks of 1.67 to 2.17 ppm (1- and 3-hydrogens of cyclopropane) and a peak towards 11.25 ppm (mobile hydrogen of acid function).

Analysis: $C_8H_{10}Br_4O_2$; molecular weight = 457.804 Calculated: %C: 20.99; %H: 2.20; %Br: 69.82; Found: %C: 20.9; %H: 2.2; %Br: 70.2.

STEP B: (1R, cis) 2,2-dimethyl-3-(1',2',2',2'-tetrabromoethyl)-cyclopropane-1-carboxylic acid chloride A mixture of 0.2 ml of dimethylformamide, 8.5 ml of thionyl chloride and 179 ml of petroleum ether (b.p.=35°-75° C.) was heated to reflux and a mixture of 35.76 g of the product of Step A in 150 ml of methylene chloride was added thereto. The mixture was refluxed with stirring for 2 hours and was then cooled and evaporated to dryness. The residue was taken up in toluene and the mixture was evaporated to dryness under reduced pressure to obtain 38 g of raw (1R,cis) 2,2-dimethyl-3-(1',2',2',2'-tetrabromoethyl)-cyclopropane-1-carboxylic acid chloride with a melting point of 88° C. which was used as is for the next step.

STEP C: 3,4,5,6-tetrahydrophthalimidomethyl (1R, cis) 2,2-dimethyl-3-(1',2',2',2'-tetrabromoethyl)-cyclopropane-1-carboxylate 3 g of pyridine were added with stirring at 0° C. to a mixture of 7.7 g of the product of Step B, 2.9 g of neopynaminol and 50 ml of anhydrous benzene and the temperature was permitted to return to room temperature with stirring over 18 hours. The mixture was poured into dilute hydrochloric acid and was then extracted with benzene. The organic extracts were washed with aqueous sodium bicarbonate solution and then with water until the wash water was neutral, dried over magnesium sulfate and was filtered. The filtrate was evaporated to dryness under reduced pressure to obtain 10 g of raw product which was chromatographed over silica gel. Elution with a 95-5 benzene-ethyl acetate mixture yielded 3.3 g 3,4,5,6-tetrahydrophthalimidomethyl (1R, cis) 2,2-dimethyl-3-(1',2',2',2'-tetrabromoethyl)-cyclopropane-1-carboxylate in the form of a mixture of its A and B isomers and 0.5 g of the said product in its B isomer form.

A and B isomer mixture

Specific rotation of $[\alpha]_D^{20} = -21.5° \pm 1°$ (c=1% in benzene)

Analysis: $C_{17}H_{19}Br_4NO_4$; molecular weight = 620.982 Calculated: %C: 32.88; %H: 3.08; %N: 2.25; %Br: 51.47; Found: %C: 33.8; %H: 3.2; %N: 2.1; %Br: 50.2.

U.V. Spectrum (ethanol)

Inflex. towards 218 nm $E_1^1 = 243$
Max. at 223 nm $E_1^1 = 275$; $\epsilon = 17,100$
Max. at 229 nm $E_1^1 = 269$; $\epsilon = 16,700$
Inflex. towards 238 nm $E_1^1 = 170$; $\epsilon = 10,500$
Inflex. towards 295 nm $E_1^1 = 8$

RMN Spectrum (deuterochloroform)

Peaks at 4.98–5.17 ppm (1'-hydrogen of ethyl side chain of B isomer); at 1.2–1.45 ppm (hydrogens of geminal methyls of B isomer); at 5.17–5.38 ppm (1'-hydrogen of ethyl side chain of A isomer); 1.2–1.38 ppm (hydrogens of geminal methyls of A isomer); at 1.58–2.08 ppm (hydrogens of cyclopropyl and methylenes of cyclohexyl); massive at 2.33 ppm (hydrogens of methylenes of cyclohexyl); and peaks at 5.33–5.70 ppm (hydrogens of —COOCH₂N—).

B isomer

Specific rotation of $[\alpha]_D^{20} = +72.5° \pm 2.5°$ (c=0.5% in benzene)

Analysis: $C_{17}H_{19}Br_4NO_4$; molecular weight = 620.982 Calculated: %C: 32.88; %H: 3.08; %N: 2.25; %BR: 51.47; Found: %C: 33.5; %H: 3.3; %N: 2.2; %BR: 50.1.

U.V. Spectrum (ethanol)

Inflex. towards 218 nm $E_1^1 = 248$
Max. at 223 nm $E_1^1 = 278$
Max. at 228–229 nm $E_1^1 = 272$
Inflex. towards 238 nm $E_1^1 = 172$
Inflex. towards 295 nm $E_1^1 = 7$

RMN Spectrum (deuterochloroform)

Peaks at 4.98–5.16 ppm (1'-hydrogen of ethyl side chain); 1.21–1.45 ppm (hydrogens of geminal methyls); 1.5–2 ppm (hydrogens of cyclopropyl and β-methylenes of cyclohexyl); massive at 2.38 ppm (hydrogens of methylenes of cyclohexyl); and peaks at 5.38–5.57 and 5.57–5.75 p.p.m. (hydrogens of COOCH₂N—).

EXAMPLE 41

3,4,5,6-tetrahydrophthalimidomethyl (1R, trans) 2,2-dimethyl-3-(1',2',2',2'-tetrabromoethyl)-cyclopropane-1-carboxylate

STEP A: (1R, trans) 2,2-dimethyl-3-(1',2',2',2'-tetrabromoethyl)-cyclopropane-1-carboxylic acid Using the procedure of Step A of Example 40, (1R, trans) 2,2-dimethyl-3-(2',2'-dibromovinyl)-cyclopropane-1-carboxylic acid was brominated to obtain a mixture of the A and B isomers of (1R, trans) 2,2-dimethyl-3-(1',2',2',2'-tetrabromoethyl)-cyclopropane-1-carboxylic acid.

RMN Spectrum

Peaks at 1.30 to 1.40 ppm (hydrogens of geminal methyls of cyclopropyl); at 1.65-1.74 and 1.97 to 2.37 ppm (1- and 3 hydrogens of cyclopropyl); at 4.30-4.47 and 4.47-4.65 ppm (1'-hydrogen of 1'-ethyl); at 9.63 ppm (hydrogen of carboxyl).

STEP B: (1R, trans) 2,2-dimethyl-3-(1',2',2',2'-tetrabromoethyl)-cyclopropane-1-carboxylic acid chloride Using the procedure of Step B of Example 40, the product of Step A was reacted with thionyl chloride to obtain (1R, trans) 2,2-dimethyl-3-(1',2',2',2'-tetrabromoethyl)-cyclopropane-1-carboxylic acid chloride which was used as is for the next step.

I.R. Spectrum (chloroform): absorption at 1778 $cm^{-1}$

STEP C: 3,4,5,6-tetrahydrophthalimidomethyl (1R, trans) 2,2-dimethyl-3-(1',2',2',2'-tetrabromoethyl)-cyclopropane-1-carboxylate Using the procedure of Step C of Example 40 7.7 g of the product of Step B were reacted to obtain 9.2 g of raw product which was chromatographed over silica gel. Elution was effected with a 9-1 benzene-ethyl acetate mixture and the product was taken up in petroleum ether (b.p.=40°-70° C.). The mixture was vacuum filtered and the product was dried to obtain 5.4 g of a mixture of A and B isomers of 3,4,5,6-tetrahydrophthalimidomethyl (1R, trans) 2,2-dimethyl-3-(1', 2',2',2'-tetrabromoethyl)-cyclopropane-1-carboxylate melting at 124° C. and having a specific rotation of $[\alpha]_D^{20} = -1° \pm 1°$ (c=1% in benzene).

Analysis: $C_{17}H_{19}Br_4NO_4$; molecular weight=620.982 Calculated: %C: 32.88; %H: 3.08; %Br 51.47; %N: 2.25; Found: %C: 33.1; %H: 3.2; %Br 51.1; %N: 2.1.

U.V. Spectrum (ethanol)

Max. at 224 nm $E_1^1=274$; $\epsilon=17,000$
Max. at 228 nm $E_1^1=269$; $\epsilon=16,700$
Inflex towards 235 nm $E_1^1=167$; $\epsilon=10,400$
Inflex. towards 280 nm $E_1^1=9$

RMN Spectrum (deuterochloroform)

Peaks at 1.25-1.30-1.31 ppm (hydrogens of geminal methyls); at 1.58 to 2.16 ppm (hydrogens of cyclopropyl and β-methylenes of cyclohexyl); at 2.16 to 2.5 ppm (hydrogens of α-methylenes of cyclohexyl); at 4.24-4.41 and 4.43-4.61 ppm (1'-hydrogen in 1'-position of ethyl side chain); at 5.51 and 5.55 ppm (—COOCH$_2$—N—)

EXAMPLE 42

(S) α-cyano-3-phenoxy-benzyl (1R, trans) 2,2-dimethyl-3-(2',2'-dichloro-1',2'-dibromoethyl)-cyclopropane-1-carboxylate

STEP A: (1R, trans) 2,2-dimethyl-3-(2',2'-dichloro-1',2'-dibromoethyl)-cyclopropane-1-carboxylic acid Using the procedure of Step A of Example 40, (1R, trans) 2,2-dimethyl-3-(2',2'-dichlorovinyl)-cyclopropane-1-carboxylic acid was reacted with bromine to obtain a mixture of the (A) and (B) isomers of (1R, trans) 2,2-dimethyl-3-(2',2'-dichloro-1',2'-dibromoethyl)-cyclopropane-1-carboxylic acid.

RMN Spectrum

Peaks at 1.17-1.37 ppm (hydrogens of geminal methyls of cyclopropyl); at 1.65-1.73 and 1.93-2.03 ppm (hydrogens in 1-position of cyclopropane); at 4.23-4.45 and 4.45-4.62 ppm (hydrogens of 1'-ethyl in the 3-position of cyclopropane).

STEP B: (1R, trans) 2,2-dimethyl-3-(2',2'-dichloro-1',2'-dibromoethyl)-cyclopropane-1-carboxylic acid chloride Using the procedure of Step B of Example 40, the product of Step A was reacted with thionyl chloride to obtain (1R, trans) 2,2-dimethyl-3-(2',2'-dichloro-1',2'-dibromoethyl)-cyclopropane-1-carboxylic acid chloride.

I.R. Spectrum (chloroform): absorption at 1777 $cm^{-1}$

STEP C: Mixture of (1R, 5S) 6,6-dimethyl-4(R) [(S) cyano-(3'-phenoxyphenyl)-methoxy]-3-oxa-bicyclo-(3,1,0)-hexan-2-one and (1R, 5S) 6,6-dimethyl-4(R)-[(R) cyano-(3'-phenoxyphenyl)-methoxy]-3-oxa-bicyclo-(3,1,0)-hexan-2-one A mixture of 22.5 g of (R,S) α-cyano-3-phenoxy-benzyl alcohol, 9.46 g of the lactone of (1R, 3S) cis 2,2-dimethyl-3-dihydroxymethyl-cyclopropane-1-carboxylic acid and 0.150 g of p-toluene sulfonic acid monohydrate was heated at 80° C. under a reduced pressure of $10^{-2}$ mm Hg for 2 hours and the water of reaction was removed by distillation. The mixture was cooled to 20° C. to obtain 30.7 g of a raw mixture A of (1R, 5S) 6,6-dimethyl-(4R)-[(S) cyano-(3'-phenoxyphenyl)-methoxy]-3-oxa-bicyclo-(3,1,0)-hexan-2-one and (1R, 5S) 6,6-dimethyl-4R-[(R) cyano-(3'-phenoxyphenyl)-methoxy]-3-oxa-bicyclo-(3,1,0)-hexan-2-one containing the unreacted starting material as the principal impurity.

STEP D: (1R, 5S) 6,6-dimethyl-4(R)-[(S)-cyano-(3'-phenoxyphenyl)-methoxy]-3-oxa-bicyclo-(3,1,0)-hexan-2-one Mixture A of Step C was chromatographed over silica gel and was eluted with a 95-5 benzene-ethyl acetate mixture to obtain 10.9 g of (1R, 5S) 6,6-dimethyl-4(R)-[(S)-cyano-(3'-phenoxyphenyl)-methoxy]-3-oxa-bicyclo-(3,1,0)-hexan-2 are melting at 126° C. and having a specific rotation of $[\alpha]_D^{20} = -71°$ (c=1% in benzene).

STEP E: (S) α-cyano-3-phenoxy-benzyl alcohol

A mixture of 10 g of the product of Step D, 1 g of p-toluene sulfonic acid monohydrate, 100 ml of dioxane and 50 ml of water was refluxed for 23 hours and was then evaporated under reduced pressure while adding ether to the initial volume. The mixture was stirred and decanted and the organic phase was washed with water, dried and evaporated to dryness under reduced pressure. The 9.5 g of residue was chromatographed over silica gel and was eluted with a 9-1 benzene-ethyl acetate mixture to obtain 6.1 g of (S) α-cyano-3-phenoxy-benzyl alcohol with a specific rotation of $[\alpha]_D^{20} = -16.5° \pm 1.5°$ (c=0.8% in benzene).

RMN Spectrum (deuterochloroform)

Peak at 3.25 ppm (hydrogen of alcohol group); at 5.42 ppm (hydrogen of carbon with nitrile attached thereto).

STEP F: (S) α-cyano-3-phenoxy-benzyl (1R, trans) 2,2-dimethyl-3-(2',2'-dichloro-1',2'-dibromoethyl)-cyclopropane-1-carboxylate A mixture of 4.45 g of the product of Step B, 2.6 g of (S) α-cyano-3-phenoxy-benzyl alcohol and 100 ml of anhydrous benzene was cooled to 15° C. and a solution of 5 ml of pyridine in 20 ml of anhydrous benzene was added thereto. The mixture was stirred for 3 hours at room temperature and was then poured into 100 ml of 2 N hydrochloric acid. The organic phase was washed with water and evaporated to dryness under reduced pressure. The residue was chromatographed over silica gel and was eluted with benzene to obtain 4.9 g of a mixture of the (A) and (B) isomers of (S) α-cyano-3-phenoxy-benzyl (1R, trans) 2,2-dimethyl-3-(2',2'-dichloro-1',2'-dibromoethyl)-cyclopropane-1-carboxylate with a specific rotation of $[\alpha]_D^{20} = 0°$ (c=1% in benzene).

Analysis: $C_{22}H_{19}Cl_2O_3N$; molecular weight=576.12
Calculated: %C: 45.86; %H: 3.32; %Br: 27.74; %Cl: 12.31; %N: 2.43; Found: %C: 46.0; %H 3.4; %Br: 27.5; %Cl: 12.2; %N: 2.2.

Circular dichroism

Max. at 287 nm $\Delta^\epsilon = +0.12$
Max. at 282 nm $\Delta^\epsilon = +0.11$
Max. at 265 nm $\Delta^\epsilon = +0.042$ RMN Spectrum Peaks at 1.20-1.26-1.31 ppm (hydrogens of geminal methyls); at 4.20-4.35 and at 4.36-4.52 ppm (1'-hydrogen of ethyl side chain); at 1.68 to 1.78, 1.97 to 2.07 and 1.97 to 2.42 ppm (hydrogens of cyclopropyl); at 6.42 ppm (hydrogen of —COOCHCN); and at 6.92 to 7.58 ppm (hydrogens of aromatic ring).

STEP G: Separation of isomers 4.69 g of the mixture of Step F were chromatographed over silica gel and was eluted with a 30-12-0.4-1.2-0.03 hexane-pentane-ether-acetonitrile-isopropanol mixture to obtain 1.385 g of isomer A of (S) α-cyano-3-phenoxy-benzyl (1R, trans) 2,2-dimethyl-3-(2',2'-dichloro-1',2'-dibromoethyl)-cyclopropane-1-carboxylate with a specific rotation of $[\alpha]_D^{20} = +35.5° \pm 2.5°$ (c=0.5% in benzene) and 0.980 g of the B isomer of the said ester with a specific rotation of $[\alpha]_D^{20} = -17.5° \pm 2°$ (c=0.8% in benzene).

EXAMPLE 43

(S) α-cyano-3-phenoxy-benzyl (1R, cis) 2,2-dimethyl-3-(2',2'-dibromo-1',2'-dichloroethyl)-cyclopropane-1-carboxylate STEP A: (1R, cis) 2,2-dimethyl-3-(2',2'-dibromo-1',2'-dichloroethyl)-cyclopropane-1-carboxylic acid 11.8 g of chlorine were bubbled into 30 ml of carbon tetrachloride at −15° C. and then a solution of 24 g of (1R, cis) 2,2-dimethyl-3-(2',2'-dibromovinyl)-cyclopropane-1-carboxylic acid in 37 ml of methylene chloride was slowly added thereto at −10° C. The mixture was stirred at 0° C. for 90 minutes and then at 25° C. for 2 hours and was then evaporated to dryness under reduced pressure. The residue was crystallized from carbon tetrachloride to obtain 7.4 g of a mixture of the (A) and (B) isomers of (1R, cis) 2,2-dimethyl-3-(2',2'-dibromo-1',2'-dichloroethyl)-cyclopropane-1-carboxylic acid melting at 134° C.

RMN Spectrum

Peaks at 1.32-1.44 and 1.28-1.48 ppm (hydrogens of geminal methyls of cyclopropane), at 5.08-5.45 and 4.67-5.0 ppm (1'-hydrogen of ethyl side chain); at 10.1 ppm (carboxyl hydrogen).

STEP B: (1R, cis) 2,2-dimethyl-3-(2',2'-dibromo-1',2'-dichloroethyl)-cyclopropane-1-carboxylic acid chloride Using the procedure of Step B of Example 40, the product of Step A was reacted with thionyl chloride to obtain (1R, cis) 2,2-dimethyl-3-(2',2'-dibromo-1',2'-dichloroethyl)-cyclopropane-1-carboxylic acid chloride which was used as is for the next step.

STEP C: (S) α-cyano-3-phenoxy-benzyl (1R, cis) 2,2-dimethyl-3-(2',2'-dibromo-1',2'-dichloroethyl)-cyclopropane-1-carboxylate A solution of 4 ml of pyridine in 20 ml of anhydrous benzene was added at 15° C. to a mixture of 3.8 g of the product of Step B, 2.5 g of (S) α-cyano-3-phenoxy-benzyl alcohol and 100 ml of anhydrous benzene and the mixture was stirred at room temperature for 4 hours and was then poured into 100 ml of 2 N hydrochloric acid. The organic phase was washed with water, dried and evaporated to dryness under reduced pressure. The residue was chromatographed over silica gel and was eluted with a 10-2 petroleum ether (b.p.=40°-70° C.)-isopropyl ether mixture to obtain 1.8 g of the (A) isomer of (S) α-cyano-3-phenoxy-benzyl (1R, cis) 2,2-dimethyl-3-(2',2'-dibromo-1',2'-dichloroethyl)-cyclopropane-1-carboxylate with Rf=0.30 and a specific rotation of $[\alpha]_D^{20} = -21° \pm 1°$ (c=1% in benzene) and 1.4 g of the (B) isomer of the said ester with an Rf=0.25 and a specific rotation of $[\alpha]_D^{20} = +80° \pm 2.5°$ (c=1% in benzene).

| Circular Dichroism - isomer A | |
| --- | --- |
| Max. at 300 nm | $\Delta^\epsilon = -0.003$ |
| Max. at 288 nm | $\Delta^\epsilon = +0.29$ |
| Max. at 264 nm | $\Delta^\epsilon = +0.11$ |
| Max. at 232 nm | $\Delta^\epsilon = -1.8$ |

RMN Spectrum (deuterochloroform)—isomer A

Peaks at 1.28-1.37 ppm (hydrogens of geminal methyls); at 5.05-5.10-5.18-5.23 ppm (1'-hydrogen of ethyl side chain); at 1.83-2.10 ppm (hydrogens of cyclopropyl); at 6.38 ppm (hydrogen of —COOCHCN); at 6.92 to 7.55 ppm (hydrogens of aromatic ring).

| Circular Dichroism - isomer B | |
| --- | --- |
| Max. at 288 nm | $\Delta^\epsilon = +0.22$ |
| Inflex. towards 263 nm | $\Delta^\epsilon = +0.62$ |
| Max. at 220 nm | $\Delta^\epsilon = +3.7$ |

RMN Spectrum (deuterochloroform)—isomer B

Peaks at 1.23-1.38 ppm (hydrogens of geminal methyls); at 4.6 to 4.95 ppm (1'-hydrogen of ethyl side chain);

at 1.75 to 2.16 ppm (hydrogens of cyclopropyl); at 6.38 ppm (hydrogen of —COOCHCN); at 6.88 to 7.57 ppm (hydrogens of aromatic ring).

EXAMPLE 44

(S) α-cyano-3-phenoxy-benzyl (1R, cis) 2,2-dimethyl-3-(1',2',2',2'-tetrachloroethyl)-cyclopropane-1-carboxylate STEP A: (1R, cis) 2,2-dimethyl-3-(1',2',2',2'-tetrachloroethyl)-cyclopropane-1-carboxylic acid 11.8 g of chlorine were dissolved in 30 ml of carbon tetrachloride and a solution of 16.7 g of (1R, cis) 2,2-dimethyl-3-(2',2'-dichlorovinyl)-cyclopropane-1-carboxylic acid in 40 ml of methylene chloride was added thereto at 0° C. over 30 minutes. The mixture was stirred at 0° C. for 24 hours and the temperature was raised to 25° C. The mixture was stirred at 25° C. for 3 hours and excess chlorine was removed by bubbling nitrogen through the mixture. The mixture was evaporated to dryness under reduced pressure and the residue was chromatographed over silica gel. The product was eluted with an 8-2 cyclohexane-ethyl acetate mixture and was crystallized from petroleum ether (b.p.=35°-75° C.) to obtain 3.14 g of (1R, cis) 2,2-dimethyl-3-(1',2',2',2'-tetrachloroethyl)-cyclopropane-1-carboxylic acid melting at 144° C.

Analysis: $C_8H_{10}Cl_4O_2$; molecular weight=279.98 Calculated: %C: 34.3; %H: 3.6; %Cl: 50.6; Found: %C: 34.4; %H: 3.7; %Cl: 50.3.

RMN Spectrum (deuterochloroform)

Peaks at 1.26–1.42 ppm and 1.30–1.42 ppm (hydrogens of geminal methyls); at 4.67–5.17 ppm and 5.08 to 5.43 ppm (1'-hydrogen of ethyl side chain); at 1.67 to 2.0 ppm (hydrogens of cyclopropyl); at 10.2 ppm (hydroxyl of carboxyl).

STEP B: (1R, cis) 2,2-dimethyl-3-(1',2',2',2'-tetrachloroethyl)-cyclopropane-1-carboxylic acid chloride 6.75 g of the product of Step A were added to a mixture of 8.7 ml of thionyl chloride and 60 ml of petroleum ether (b.p.=35°-70° C.) and the mixture was refluxed for 4½ hours and was then evaporated to dryness under reduced pressure. The residue was taken up in benzene and the mixture was evaporated to dryness to obtain raw (1R, cis) 2,2-dimethyl-3-(1',2',2',2'-tetrachloroethyl)-cyclopropane-1-carboxylic acid chloride which was used as is for the next step.

STEP C: (S) α-cyano-3-phenoxy-benzyl (1R, cis) 2,2-dimethyl-3-(1',2',2',2'-tetrachloroethyl)-cyclopropane-1-carboxylate 3 ml of pyridine were slowly added to a mixture of 3.19 g of the product of Step B, 2.6 g of (S) α-cyano-3-phenoxy-benzylalcohol and 30 ml of anhydrous benzene cooled in an ice bath and the mixture was stirred for 24 hours at room temperature and was then poured into cold dilute hydrochloric acid. The mixture was extracted with benzene and the organic phase was washed with aqueous sodium bicarbonate solution, then with water, dried over sodium sulfate and filtered. The filtrate was evaporated to dryness under reduced pressure and the residue was chromatographed over silica gel. Elution with a 7-3 benzene-cyclohexane mixture yielded 2.258 g of the (A) isomer of (S) α-cyano-3-phenoxy-benzyl (1R, cis) 2,2-dimethyl-3-(1',2',2',2'-tetrachloroethyl)-cyclopropane-1-carboxylate with a specific rotation of $[\alpha]_D^{20}=+35.5°\pm2°$ (c=0.6% in benzene) and 1.48 g of a mixture of the (A) and (B) isomers of the said ester with a specific rotation of $[\alpha]_D^{20}=-33.5°\pm2.5°$ (c=0.4% in benzene).

Analysis: $C_{22}H_{19}Cl_4NO_3$; molecular weight=487.213 Calculated: %C: 54.23; %H: 3.93; %N: 2.87; %Cl: 29.1; A isomer Found: %C: 54.4; %H: 3.8; %N: 2.8; %Cl: 28.5; A & B isomer Found: %C: 54.5; %H: 3.9; %N: 2.8; %Cl: 28.8.

RMN Spectrum (deuterochloroform)—(A) isomer

Peaks at 1.28–1.37 ppm (hydrogens of geminal methyls); at 1.75 to 2.08 ppm (hydrogens of cyclopropyl); at 5.07 to 5.25 ppm (1'-hydrogen of ethyl side chain); at 6.35 ppm (hydrogens of —COOCHCN); at 6.92 to 7.58 ppm (hydrogens of aromatic ring).

RMN Spectrum (deuterochloroform)-(A) and (B) isomer mixture

Peaks at 1.2–1.35 ppm (hydrogens of geminal methyls of R isomer); at 1.27–1.35 ppm (hydrogens of geminal methyls of isomer S); at 1.75–2.08 ppm (hydrogens of cyclopropyl); at 4.77 to 4.94 ppm (1'-hydrogen of ethyl side chain); at 5.08 to 5.26 ppm (1'-hydrogen of ethyl side chain); at 6.35 to 6.37 ppm (hydrogen of —COOCHCN); at 7.93 to 7.58 ppm (hydrogens of aromatic ring).

EXAMPLE 45

(R) α-cyano-3-phenoxy-benzyl (1R, trans) 2,2-dimethyl-3-(1',2'-dibromo-2',2'-dichloroethyl)-cyclopropane-1-carboxylate STEP A: (R) α-cyano-3-phenoxybenzyl alcohol The mixture of Step C of Example 42 was chromatographed to obtain 7.32 g of (1R, 5S) 6,6-dimethyl-4(R)-[(R)-cyano-(3'-phenoxy-phenyl)-methoxy]-3-oxa-bicyclo-(3,1,0)-hexan-2-one with a specific rotation of $[\alpha]_D^{20}=-120°\pm2.5°$ (c=0.9% in benzene). 12.8 g of the said product were reacted as in Step E of Example 42 to obtain after chromatographic purification 5 g of (R) α-cyano-3-phenoxybenzyl alcohol with a specific rotation of $[\alpha]_D^{20}=11°\pm2°$ (c±0.5% in benzene).

STEP B: (R) α-cyano-3-phenoxy-benzyl (1R, trans) 2,2-dimethyl-3-(1',2'-dibromo-2',2'-dichloroethyl)-cyclopropane-1-carboxylate Using the procedure of Step F of Example 42, 2 g of (1R, trans) 2,2-dimethyl-3-(1',2'-dibromo-2',2'-dichloroethyl)-cyclopropane-1-carboxylic acid chloride and 1.1 g of (R) α-cyano-3-phenoxybenzyl alcohol were reacted to obtain 1.4 g of a mixture of the (A) and (B) isomers of (R) α-cyano-3-phenoxybenzyl (1R, trans) 2,2-dimethyl-3-(1',2'-dibromo-2',2'-dichloroethyl)-cyclopropane-1-carboxylate with a specific rotation of $[\alpha]_D^{20}=-28°\pm2°$ (c=0.7% in benzene.

Analysis: $C_{22}H_{19}Br_2Cl_2NO_3$; molecular weight=576.122 Calculated: %C: 45.87; %H: 3.32; %N 2.43; %Cl: 12.31; %Br: 27.74; Found: %C: 46.3; %H: 3.3; %N: 2.4; %Cl: 12.4; %Br: 27.4.

RMN Spectrum (deuterochloroform)

Peaks at 1.31–1.35 ppm (hydrogens of geminal methyls); at 1.66 to 2.42 ppm (hydrogens of cyclopropyl); at 4.23–4.42 ppm and 4.42–4.58 ppm (1'-hydrogen of ethyl side chain); at 6.47 ppm (hydrogen of —COOCHCN); at 6.92 to 7.58 ppm (hydrogens of aromatic ring).

Circular Dichroism (dioxane)

Max. at 219 nm $\epsilon = -5.4$
Max. at 280 nm $\epsilon = -0.28$
Inflex. towards 285 nm $\epsilon = -0.27$ The mixture of A and B isomers was chromatographed over silical gel and was eluted with a 7-2.8-0.17 hexane-pentane-ether mixture to separate the A and B isomers.

RMN Spectrum (deuterochloroform): isomer A

Peaks at 1.32–1.37 ppm (hydrogens of geminal methyls); at 1.66–1.76 ppm and 2.08–2.17 ppm and 2.26–2.35 ppm (hydrogens of cyclopropyl); at 4.2–4.37 ppm (1'-hydrogen of ethyl side chain); at 6.42 ppm (hydrogen of —COOCHCN); at 6.92 to 7.58 ppm (hydrogens of aromatic ring).

RMN Spectrum (deuterochloroform): isomer B

Peaks at 4.37–4.53 (1'-hydrogen of ethyl side chain).

EXAMPLE 46

An emulsifiable concentrate was prepared in the form of a homogeneous mixture of 0.25 g of the A isomer of (S) α-cyano-3-phenoxy-benzyl 2,2-dimethyl-3S-(1',2'2',2'-tetrabromoethyl)-cyclopropane-1R-carboxylate, 1 g of piperonyl butoxide, 0.25 g of Tween80, (polyoxyethylene derivative partial esters of fatty acids) 0.1 g of Topanol A and 98.4 g of water.

Another emulsifiable concentrate was prepared containing 0.015 g of the same said A isomer or of (S) α-cyano-3-phenoxy-benzyl (1R, trans) 2,2-dimethyl-3-(1';2'-dibromo-2', 2'-dichloroethyl)-cyclopropane-1-carboxylate, 0.5 g of piperonyl butoxide, 0.1 g of Topanol A and 99.385 g of xylene. A third emulsifiable concentrate was prepared containing 1.5 g of the same said A isomer or of (S) α-cyano-3-phenoxy-benzyl (1R, trans) 2,2-dimethyl-3-(1',2'-dibromo-2',2'-dichloroethyl)-cyclopropane-1-carboxylate, 20 g of Tween 80, 0.1 g of Topanol A and 78.4 g of xylene.

EXAMPLE 47

A fumigant composition was prepared comprising 0.25 g of the A isomer of (S) α-cyano-3-phenoxy-benzyl 2,2-dimethyl-3S-(1',2',2',2'-tetrabromoethyl)-cyclopropane-1R-carboxylate, 25 g of tabu powder, 40 g of cedar leaf powder, 33.75 g of pine sawdust, 0.5 g of brilliant green and 0.5 g of p-nitrophenol.

EXAMPLE 48

An insecticide composition was prepared from 1 g of (R,S) α-cyano-3-phenoxy-benzyl dl cis-trans 2,2-dimethyl-3-(1',2'-dibromo-2',2'-dichloroethyl)-cyclopropane-1-carboxylate, 8 g of piperonyl butoxide, 1 g of Tween 80, 0.1 g of Topanol A and 89.9 g of water.

EXAMPLE 49

An emulsifiable concentrate useful as an acaricide was prepared from 20 parts by weight of (S) α-cyano-3-phenoxy-benzyl 2,2-dimethyl-3S-(1',2',2',2'-tetrabromoethyl)-cyclopropane-1R-carboxylate or of (S) α-cyano-3-phenoxy-benzyl 1R, trans 2,2-dimethyl-3-(2',2'-dichloro-1',2'-dibromoethyl)-cyclopropane-1-carboxylate, 6.5 parts by weight of Atlox 4851 (oxyethylene triglyceride with a sulfonate-acid index of 1.5), 3.3 parts by weight of Atlox 4855 (oxyethylene triglyceride with a sulfonate-acid index of 3) and 70.2 parts by weight of xylene.

EXAMPLE 50

A nematocidal composition in the form of an emulsifiable concentrate for the treatment of soil contained, by weight, 45 parts of (S) α-cyano-3-phenoxy-benzyl-2,2-dimethyl-3S-(1',2',2',2'-tetrabromoethyl)-cyclopropane-1R-carboxylate or of (S) α-cyano-3-phenoxy-benzyl (1R, trans) 2,2-dimethyl-3-(2',2'-dichloro 1',2'-dibromoethyl) cyclopropane-1-carboxylate, 6.4 parts of Atlox 4851, 3.2 parts of Atlox 4855 and 45.4 parts of xylene.

EXAMPLE 51

An ixodicide composition was prepared from 0.5 g of an equimolar mixture of the A and B isomers of (S) α-cyano-3-phenoxy-benzyl 2,2-dimethyl-3S-(1',2',2',2'-tetrabromoethyl)-cyclopropane-1R-carboxylate or of (S) α-cyano-3-phenoxy benzyl (1R, trans) 2,2-dimethyl-3(2',2'-dichloro 1',2'-dibromo ethyl) cyclopropane-1-carboxylate, 25 g of Triton X100, 10 g of Polysorbate 80, 1 g of α-tocopherol acetate and sufficient ethanol for 100 ml of mixture. The composition after dilution with 50 volumes of water was used externally.

An injectable ixodicide composition was prepared from 2 g of an equimolar mixture of the A and B isomers of (S) α-cyano-3-phenoxy-benzyl 2,2-dimethyl-3R-(1',2',2',2'-tetrabromoethyl)-cyclopropane-1R-carboxylate or of (S) α-cyano-3-phenoxy benzyle (1R, trans) 2,2-dimethyl-3-(2',2'-dichloro 1',2'-dibromoethyl) cyclopropane-1-carboxylate, 6.65 g of piperonyl butoxide, 0.33 g of α-tocopherol acetate and sufficient oily excipient to obtain a final volume of 100 ml. The oily excipient was 29 g of benzyl benzoate in arachide oil for a final volume of 100 ml.

EXAMPLE 52

A feed base containing a minimum of 11% of raw protein material (2.8% of urea), 2.5% of grass material and a maximum of 15% of cellulosic material, 6% of mineral material and 13% moisture correspond to 82 forage units per 100 kilos and also contained per 100 kilos 910,000 I.U. of vitamin A, 91,000 I.U. of vitamin $D_3$, 156 mg of vitamin E and 150 mg of vitamin C. The feed base was prepared from corn, dehydrated alfalfa, wheat stalks, palm oil molasses press cake, urea and mineral vitamin condiment. To form an animal feed, 0.04 kg of an equimolar mixture of the A and B isomers of (S) α-cyano-3-phenoxy-benzyl 2,2-dimethyl-3S-(1',2',2',2'-tetrabromoethyl)-cyclopropane-1R-carboxylate or of (S) α-cyano-3-phenoxy-benzyl (1R, trans) 2,2-dimethyl 3-(2',2'-dichloro 1',2'-dibromoethyl) cyclopropane-1-carboxylate was added to the feed base.

EXAMPLE 53

An antifungal solution was prepared from 50 g of the A and B isomers of (S) α-cyano-3-phenoxy-benzyl 2,2-dimethyl-3S-(1',2',2',2'(R,S)-tetrabromoethyl)-cyclopropane-1R-carboxylate, 80 g of Emcol H 300 B (mixture of calcium salt of alkyl benzene sulfonic acid and polyoxyethylene ethers) and 870 g of xylene.

An antifungal wettable powder was prepared from 20 g of the A and B isomers of (S) α-cyano-3-phenoxy-benzyl 2,2-dimethyl-3S-(1',2'(R,S)-dibromo-2',2'-dichloroethyl)-cyclopropane-1R-carboxylate 15 g of Ekapersol S (condensation product of sodium naphthalene sulfonate), 0.5 g of Brecolane NVA (sodium alkyl naphthalene sulfonate), 3.95 g of Zeosil 39 (precipitated synthetic hydrated silica) and 25 g of Vercoryl S (colloidal Kaolin).

PESTICIDAL TEST DATA

The following compounds were used in the insecticidal tests: A and B isomers of (S) α-cyano-3-phenoxy-benzyl 2,2-dimethyl-3S-(1',2',2',2'-tetrabromoethyl)-cyclopropane-1R-carboxylate [products $Y_1$ and $Y_2$, respectively], the A and B isomers of (S) α-cyano-3-phenoxy-benzyl 2,2-dimethyl-3S-(1',2'-dibromo-2',2'-dichloroethyl)-cyclopropane-1R-carboxylate [products $Y_3$ and $Y_4$, respectively], (R,S) α-cyano-3-phenoxy-benzyl dl cis-trans 2,2-dimethyl-3-(1',2'-dibromo-2',2'-dichloroethyl)-cyclopropane-1-carboxylate [product $Y_5$], (R,S) α-cyano-3-phenoxy-benzyl 2,2-dimethyl-3R-(1',2',2',2'-tetrabromoethyl)-cyclopropane-1R-carboxylate [product $Y_6$], (R,S) α-cyano-3-phenoxy-benzyl 2,2-dimethyl-3S-)1',2'-dichloro-2',2'-dibromoethyl)-cyclopropane-1R-carboxylate [product $Y_7$], (R,S) α-cyano-3-phenoxy-benzyl 2,2-dimethyl-3R-(1',2'-dibromo-2',2'-dichloroethyl)-cyclopropane-1R-carboxylate [product $Y_8$], 5-benzyl-3-furyl-methyl 2,2-dimethyl-3S-(1',2°,2',2'-tetrabromoethyl)-cyclopropane-1R-carboxylate [product $Y_9$], (S) α-cyano-3-phenoxy-benzyl (1R, trans) 2,2-dimethyl-3-(1',2'-dibromo-2',2'-dichloroethyl)-cyclopropane-1-carboxylate [product $Y_{10}$], A isomer or (S) α-cyano-3-phenoxy-benzyl (1R, cis) 2,2-dimethyl-3-(1',2'-dichloro-2',2'-dibromoethyl)-cyclopropane-1-carboxylate [product $Y_{11}$] and the B isomer of said (1R, cis) compound [product $Y_{12}$].

A. Lethal activity against household flies

The test insects were 4 days old female houseflies which received a topical application of 1 μl of an acetone solution of the test compound to the dorsal thorax with the aid of an Arnold micromanipulator. 50 insects were used for each test and the number of dead insects after 24 hours was determined. The test compounds were used with and without 10 parts of piperonyl butoxide synergist per part of test compound. The results were expressed in $LD_{50}$ on the dose in nanograms necessary to kill 50% of the insects and the results are reported in Table I.

TABLE I

| Compound | $LD_{50}$ in ng/insect | |
|---|---|---|
| | with synergist | without synergist |
| $Y_1$ | 0.24 | 1.13 |
| $Y_2$ | 0.55 | 1.0 |
| $Y_3$ | 0.83 | 1.25 |
| $Y_4$ | 0.46 | 0.60 |
| $Y_7$ | 0.99 | 2.03 |
| $Y_{10}$ | 0.91 | 5.75 |
| $Y_{11}$ | 0.88 | 1.67 |
| $Y_{12}$ | 0.82 | 2.95 |

The results of Table I show that the tested compounds have an extremely elevated lethal activity against the house fly which is even more elevated with an addition of piperonyl butoxide as a synergist.

B. Lethal activity against larvae of Spodoptera littoralis

The tests were effected by topical application of an acetone solution of the test compound with an Arnold micromanipulator to the dorsal thorax of larvae of Spodoptera littoralis using 10 to 15 larvae for each dose. The larvae were in the 4th stage of larvae development which were about 10 days old and were kept at 24° C. and 65% relative humidity. After treatment, the larvae were placed in an artifical nutritive media (Poitoit medium) and the number of dead was determined after 48 hours to ascertain the $LD_{50}$ and the results are reported in Table II.

TABLE II

| Compound | $LD_{50}$ in ng |
|---|---|
| $Y_1$ | 0.68 |
| $Y_2$ | 0.32 |

The results of Table II show that the products had a extremely high lethal activity against the larvae of Spodoptera littoralis.

C. Insecticidal Activity against Spodoptera littoralis caterpillars

The test was effected by topical application of 1μ of an acetone solution of the test compound to the dorsal thorax of each caterpillar using 15 individuals of Spodoptera littoralis in the 4th larva stage for each dose. After treatment, the individuals were placed in an artifical nutritive (Poitoit medium) and the number of dead were determined 24 and 48 hours later to ascertain the $LD_{50}$ dose in ng. The results are reported in Table III.

TABLE III

| Compound | Mg of active material per liter in ng/caterpillar | % efficacity 24 Hours | % efficacity 48 Hours | $LD_{50}$ after 48 Hours in ng/caterpillar |
|---|---|---|---|---|
| Equimolar mixture of $Y_1$ and $Y_2$ | 0.5 | 80.0 | 66.7 | |
| | 0.375 | 53.3 | 40.0 | |
| | 0.25 | 33.3 | 33.3 | 0.38 |
| | 0.125 | 0 | 0 | |
| Equimolar mixture of $Y_3$ and $Y_4$ | 0.5 | 100 | 100 | |
| | 0.375 | 76.7 | 73.3 | |
| | 0.25 | 40.0 | 40.0 | 0.31 |
| | 0.125 | 49.3 | 20.0 | |
| $Y_7$ | 2.5 | | 100 | |
| | 1.25 | | 66.6 | |
| | 0.625 | | 53.3 | 0.51 |
| | 0.312 | | 40.0 | |
| | 1 | | 93.2 | |
| | 0.75 | | 66.6 | |
| $Y_9$ | 0.50 | | 46.6 | 0.51 |
| | 0.25 | | 13.3 | |
| $Y_{10}$ | | | | 0.22 |
| $Y_{11}$ | | | | 0.57 |
| $Y_{12}$ | | | | 0.65 |

The results of Table III show that the test compounds had a very high insecticidal activity against Spodoptera littoralis.

D. Knock Down Activity against House Flies

Female house flies about 4 day old were directly sprayed in a Kearns and March chamber with a solution of 1 g/l of the test compound in a 1—1 acetone-kerosene mixture using 0.2 ml twice. 50 insects were used for each test. The readings were effected each minute for 10 minutes and then at 15 minutes. The $KT_{50}$ was determined by the usual methods and the results are reported in Table IV.

TABLE IV

| Compound | $KT_{50}$ in minutes |
|---|---|
| $Y_1$ | 3.5 |
| $Y_2$ | 6.5 |
| $Y_3$ | 4.5 |
| $Y_4$ | 4.2 |

TABLE IV-continued

| Compound | $KT_{50}$ in minutes |
|---|---|
| $Y_{10}$ | 6.00 |
| $Y_{11}$ | 6.12 |
| $Y_{12}$ | 6.02 |

The $KT_{50}$ is the time required to knock down 50% of the insects with a fixed dose of the tested product as the time is inversely proportional to the rapid action of the product. The results of Table IV show that the tested compounds possess an interesting knock down activity.

E. Insecticidal Activity against Larvae of *Epilachna Varivestris*

The test was effected by topical application of the test compound as in test C above with penultimate larval stage of *Epilachna Varivestris* and after treatment, the larvae were fed bean plants. The number of dead was determined 72 hours after treatment and the results are reported in Table V.

TABLE V

| Compound | Doses in mg/l | % of Mortality | $LD_{50}$ in ng/insect |
|---|---|---|---|
| | 1.25 | 100 | |
| | 1 | 90 | |
| $Y_3$ | 0.625 | 60 | 0.37 |
| | 0.312 | 50 | |
| | 1 | 90.0 | |
| | 0.625 | 80.0 | |
| $Y_4$ | 0.312 | 70.0 | 0.20 |
| | 0.156 | 40.0 | |
| | 5 | 100 | |
| | 2.5 | 80 | |
| $Y_5$ | 1.25 | 70 | 0.53 |
| | 0.625 | 50 | |
| $Y_{10}$ | | | 0.18 |
| $Y_{11}$ | | | 4.26 |
| $Y_{12}$ | | | 6.95 |
| | 2.5 | 90 | |
| | 1.25 | 80 | |
| $Y_6$ | 0.625 | 60 | 0.44 |
| | 0.312 | 40 | |
| | 5 | 100 | |
| | 2.5 | 90 | |
| $Y_7$ | 1.25 | 50 | 0.93 |
| | 0.625 | 40 | |
| | 5 | 100 | |
| | 2.5 | 80 | |
| $Y_8$ | 1.25 | 60 | 0.88 |
| | 0.625 | 40 | |
| | 0.312 | 20 | |

F. Insecticidal Activity against *Sitophilus Granarius* and *Tribolium Castaneum*

The test was effected by direct spraying of infested wheat with 5 ml of an acetone solution of the test product and 0.1 ml of water per 100 g of wheat contained in a one liter flask in a rotating (movement) evaporator. The wheat was artificially infested with 50 individuals of either *Sitophilus Granarius* or *Tribolium Castaneum* and the percentage of dead for each dose was determined after 7 days as compared to untreated controls. The average results for 100 insects was used to determine the $LC_{50}$ (lethal concentration) which is reported in Table VI.

TABLE VI

| Compounds | Doses in ppm | % efficacity in 7 days Sitophilus Granarius | Tribolium Castaneum | $LC_{50}$ in ppm for Sitophilus | $LC_{50}$ in ppm for Tribolium |
|---|---|---|---|---|---|
| Equimolar mixture of $Y_1$ and $Y_2$ | 1 | 67.0 | 100.0 | | |
| | 0.5 | 28.7 | 92.0 | 0.75 | 0.32 |
| | 0.25 | 4.0 | 24.3 | | |
| Equimolar mixture of $Y_3$ and $Y_4$ | 1 | 62.5 | 100.0 | | |
| | 0.5 | 18.4 | 99.0 | 0.85 | 0.22 |
| | 0.25 | 2.0 | 62.6 | | |
| $Y_{10}$ | 1.5 | 90 | 100 | | |
| | 1.0 | 66.70 | 96.9 | | |
| | 0.75 | 35.3 | 89.5 | 0.80 | 0.19 |
| | 0.5 | 18.2 | 85.3 | | |
| | 0.25 | 2.0 | 62.0 | | |

Natural mortality for Controls: Sitophilus 1.0%
Tribolium 4.0%

The results of Table VI show that the tested products have a strong insecticidal for Tribolium Castaneum and only a slightly lower insecticidal activity against Sitophilus Granarius.

G. Insecticidal Activity against *Blatella Germanica*

The test effected was affected as a film on glass by placing 2 ml of an acetone solution of 10 mg/l of the test product with a Petri dish of 154 cm² and then the acetone was evaporated to form a film of 1.3 mg of test compound per square meter. Adult, male *Blatella Germanica* were placed on the film and the number of dead insects was determined after 5,10,15,20,25,30,40,50 and 60 minutes. The insects were withdrawn from the Petri dish and transferred to a clean wide mouth bottle. The percent of mortality was determined after 24, 48 and 72 hours with respect to the untreated controls and the results are reported in Table VII.

TABLE VII

| Compound | Active Material in mg/l | % Dead (K.D.) | | | | | | | | | % Mortality | | |
|---|---|---|---|---|---|---|---|---|---|---|---|---|---|
| | | 5 mm | 10 mm | 15 mm | 20 mm | 25 mm | 30 mm | 40 mm | 50 mm | 60 mm | 24 H | 48 H | 72 H |
| Equimolar mixture of $Y_1$ and $Y_2$ | 10 | 20.0 | 40.0 | 70.0 | 75.0 | 80.0 | 85.0 | 90.0 | 100 | 100 | 95.0 | 90.0 | 95.0 |
| | 1 | 15.0 | 10.0 | 10.0 | 20.0 | 30.0 | 35.0 | 60.0 | 70.0 | 85.0 | 40.0 | 70.0 | 70.0 |
| | 0.1 | 0 | 0 | 0 | 10.0 | 10.0 | 10.0 | 15.0 | 20.0 | 30.0 | 0 | 0 | 0 |
| Equimolar mixture of $Y_3$ and $Y_4$ | 10 | 30.0 | 45.0 | 70.0 | 85.0 | 95.0 | 95.0 | 100 | 100 | 100 | 100 | 100 | 100 |
| | 1 | 5.0 | 10.0 | 35.0 | 55.0 | 60.0 | 70.0 | 70.0 | 95.0 | 100 | 50.0 | 65.0 | 65.0 |
| | 0.1 | 0 | 0 | 5.0 | 5.0 | 10.0 | 20.0 | 30.0 | 30.0 | 35.0 | 10.0 | 10.0 | 10.0 |
| Controls | | 0 | 0 | 0 | 0 | 0 | 0 | 0 | 0 | 0 | 0 | 0 | 0 |

The results of Table VII show that the test compounds have a remarkable insecticidal activity against *Blatella Germanica*.

H. Acaricidal Activity against *Tetranychus Urticae*

The test was effected on bean leaves infested with 10 female *Tetranychus Urticae* per leaf coated about its periphery with glue. The females were left for 24 hours and were then removed and the leaves infested with eggs were divided into 2 groups. The first group was treated with the test compound by spraying of each leaf with 0.5 ml of an aqueous solution with a concentration of 50 or 25 g of the test compound per hectare. The second group of leaves were not treated and served as the control. The number of adults living, eggs living, adults and living larvae was determined 9 days after the start of the treatment to ascertain the percent of mortality of the adults, eggs and larvae with respect to the controls. The results are reported in Table VIII.

TABLE VIII

| Compound | Grams of active Material per ha. | No. of laid eggs | % Mortality eggs | larvae | Adults |
|---|---|---|---|---|---|
| Equimolar mixture of $Y_1$ and $Y_2$ | 50 | 103 | 25.2 | 33.8 | |
| | 25 | 161 | 22.4 | 22.4 | |
| Equimolar mixture of $Y_3$ and $Y_4$ | 50 | 85 | 45.9 | 23.9 | |
| | 25 | 61 | 19.7 | 21.5 | |
| $Y_{10}$ | 50 | | | | |
| | 25 | | 54.3 | 47.6 | 52.3 |
| Control | 0 | 181 | 7.7 | 2.4 | |

The results of Table VIII show that the tested products possess an clear acaricidal activity against *Tetranychus Urticae*.

I. Activity against Panonychus Ulmi

The test was effected with Sirah grape vine with 4 tests for each dose by the block method with untreated control introduced into each block and each elementary parcel contained 10 vines. A single treatment was effected with a base of 1000 liters of spraying mixture per hectare with a constant pressure Van de Weij sprayer. The results were determined after 7, 16 and 26 days after treatment and the number of moving forms (larvae and adults) on 15 leaves were determined with collection by brushing and the results are expressed in relation to the untreated controls in Table IX.

TABLE IX

| Compound | dose in g/hl | moving form on 15 leaves after days 7 | 16 | 26 |
|---|---|---|---|---|
| $Y_2$ | 2.5 | 338 | 453 | 356 |
| Controls | 0 | 492 | 967 | 696 |

The results of Table IX show that the tested compound has a clear acaricidal activity against adult and larvae *Panonychus Ulmi*.

J. Hematicidal Activity against Ditylenchus Myceliophagus

The test consisted of placing 0.5 ml of water containing about 2000 nematodes into a pill machine containing 10 ml of an aqueous solution of the test compound and the degree of mortality was determined with a binocular microscope 24 hours after treatment. 3 tests were made corresponding each time to a sample of 1 ml of test solution and the results are reported in Table X.

TABLE X

| Compound | Active Material in mg/l | % Mortality |
|---|---|---|
| Equimolar mixture of $Y_1$ and $Y_2$ | 10 | 99% |
| | 1 | 23.5% |
| Equimolar mixture of $Y_3$ and $Y_4$ | 10 | 99.3% |
| | 1 | 41.5% |
| Controls | 0 | 3.2 |

The results of Table X show that the tested products have an interesting nematocidal activity against *Ditylenchus Myceliophagus*.

K. Ixodicide Activity

A solution of 0.5 g of an equimolar mixture of $Y_1$ and $Y_2$, 10 g of polysorbate 80, 25 g of Triton X 100, 1 g of atocophenol acetate and sufficient ethanol for a final volume of 100 ml was diluted just before use with 50 volumes of water to obtain a concentration of 1/10,000 parts by weight of the active ingredient.

Ticks of Rhipicephalus Sanguineus genus were withdrawn from dogs and were placed in contact for 30 minutes with the above preparation for an in vitro test. After 30 minutes, it was ascertained that the ticks were driven to uncoordinated movements and after 4 hours they were dead while the control ticks were unaffected.

In a second test, two dogs infested with ixodes of Rhipicephalus Sanguineus genus were used with the ticks being fixed principally about the head, or the ears, neck and chest. The body of each animal was soaked with the above solution at a volume of 2.5 liters per dog. The place or meeting of the animals was sprayed with the balance of the solution having served for the treatment. After 24 hours, the ticks were still fixed and still having movement and after 72 hours, the ticks were still fixed but dead. The local and general tolerance was excellent when the animals were examined 8 days after the treatment.

L. Fungistatic Activity

The fungistatic efficacy of the test product was determined by introducing 0.5 ml of a solution of the test compound and 0.5 ml of a suspension of spores of the fungus to be combatted adjusted to about 100,000 spores per ml into 4 ml of Staron nutritive media and after 7 days of incubation, readings were taken by visual observation of the development of fungus of the absence of development (0 to 100% efficacy). The Staron nutritive media consisted of 20 g of glucose, 6 g of peptone, 1 g of yeast extract, 4 g of corn steep, 0.5 g of sodium chloride, 1 g of monopotassium phosphate, 0.5 g of magnesium sulfate, 10 mg of ferrous sulfate and sufficient water for a final volume of 1 liter.

Using the said procedure, equimolar mixtures of compounds $Y_1$ and $Y_2$ and compounds $Y_3$ and $Y_4$ showed a fungistatic threshold against Fusarium Roseum and Botrytis Cinerea at 25 and 50 ppm, respectively; against Phoma Species between 25 to 50 and 10 to 25 ppm, respectively and the equimolar mixture of compounds $Y_3$ and $Y_4$ showed a fungistatic threshold against Penicillium Rosqueforti between 150 to 200 ppm. The said mixtures showed interesting antifungal activity in these tests.

M. Insecticidal Activity against Household Flies with Fumigant Serpentine

A neutral fumigant serpentine support was impregnated with a solution of product $Y_{10}$ in acetone and 20 domestic female houseflies 4 to 5 days old were released into a closed glass cylinder with a volume of 13.50 dm3. During 2 minutes, the fumigant serpentine was introduced and was consumed at one end. The knock down control was effected every minutes and the test was stopped 5 minutes after that the totality of insects was knocked down. A series of 3 tests was run for each dose and the results are reported in the following Table.

| Compound | Doses in weight of compound in Coil | KT$_{50}$ in minutes | | KT$_{50}$ Average | |
|---|---|---|---|---|---|
| Y$_{10}$ | 0.4 | 7.5 | 8.8 | 6.6 | 7.75 |
| | 0.2 | 11.8 | 10.2 | 9.2 | 10.22 |

Product Y$_{10}$, when used in fumigant form, has a good insecticidal activity.

N. Insecticidal Activity against Aedes Aegypti larvae

Wide mouth bottles of 370 ml of volume received 200 ml of water and 1 ml of an acetone solution of product Y$_{10}$ was added to each. Each bottle was infested with 10 larvae of Aedes Aegypti (last larva stage) in 49 ml of water. The degree of efficacy was determined 24 to 48 hours after the infestation and during the test, the bottles were held at 25° in an oven. The LC$_{50}$ dose was $3.24 \times 10^{-5}$ ppm and shown that product Y$_{10}$ has a strong insecticidal activity against the larvae of *Aedes Aegypti*.

O. Activity against *Blattella germanica*

This test was effected by topical application of 2 microliters of product Y$_{10}$ in an acetone solution between the second and third pair of feet of adult males of *Blattella germanica* and the insects were then kept at 20° C. in a penumbral and were feeded. The test dose were 10, 7.5, 5, 3.75 and 2.5 ng/insect and the reading were taken 24 and 48 hours and 6 days after the treatment and the LD$_{50}$ was 1.06 ng per insect which indicated a strong insecticidal activity.

P. Activity against *Dysdercus fascatus*

This test was effected by application of 1 microliter of product Y$_{10}$ in an acetone solution on the ventral thorax of each individual. The test doses were 3.75—2.5—1.-25—1—0.625 ng/insect and the degree of efficacy was determined 24 and 48 hours and 5 days after the treatment and the LD$_{50}$ was 1.06 ng per insect which indicated a strong insecticidal activity.

Various modifications of the products and processes of the invention may be made without departing from the spirit or scope thereof and it is to be understood that the invention is to be limited only as defined in the appended claims.

We claim:

1. A compound of the formula

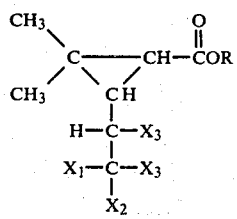

wherein X$_1$ is selected from the group consisting of hydrogen, fluorine, chlorine and bromine, X$_2$ is selected from the group consisting of fluorine, chlorine and bromine, X$_3$ is selected from the group consisting of chlorine, bromine and iodine and R is selected from the group consisting of

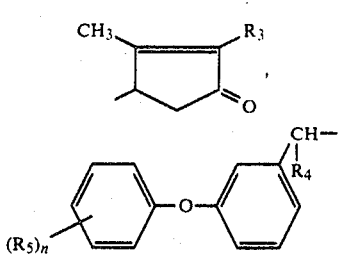

and benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogens, R$_3$ is an aliphatic of 2 to 6 carbon atoms having at least one double bond, R$_4$ is selected from the group consisting of hydrogen, —CN and —C|CH, R$_5$ is selected from the group consisting of chlorine and methyl, n is 0,1 or 2.

2. A compound of claim 1 having the 1R, cis or 1R, trans structure.

3. A compound of claim 1 having the dl-cis or dl-trans structure.

4. A mixture of compounds of claim 1 having dl-cis or dl-trans structure.

5. A compound of claim 1 wherein X$_1$ and X$_2$ are identical and are selected from the group consisting of chlorine, bromine and fluorine.

6. A compound of claim 1 wherein X$_1$ and X$_2$ are different.

7. A compound of claim 1 wherein R is selected from the group consisting of 1-oxo-2-allyl-3-methyl-cyclopent-2-en-4-yl, 3-phenoxy-benzyl, and α-cyano-3-phenoxy-benzyl in racemic or optical isomer form.

8. A compound of claim 7 wherein X$_1$ and X$_2$ are identical.

9. A compound of claim 1 which is (S)α-cyano-3-phenoxy-benzyl 2,2-dimethyl-3S-(1',2'-dibromo-2',2'-dichloroethyl)-cyclopropane-1R-carboxylate in the form of its diastereoisomers with respect to the asymetric carbon atom in the 1'-position or mixtures thereof.

10. A compound of claim 1 in the form of its diastereoisomers with respect to the asymetrical carbon atom in the 1'-position or mixtures thereof selected from the group consisting of
   (R,S)α-cyano-3-phenoxy-benzyl 2,2-dimethyl-3R-(1',2',2',2'-tetrabromoethyl)-cyclopropane-1R-carboxylate,
   (R,S)α-cyano-3-phenoxy-benzyl 2,2-dimethyl-3R-(1',2'-dibromo-2',2'-dichloroethyl)-cyclopropane-1R-carboxylate,
   (S) 1-oxo-2-allyl-3-methyl-cyclopent-2-en-4-yl 2,2-dimethyl-3R-(1',2',2',2'-tetrabromoethyl)-cyclopropane-1R-carboxylate,
   (S) 1-oxo-2-allyl-3-methyl-cyclopent-2-en-4-yl 2,2-dimethyl-3S-(1',2',2',2'-tetrabromoethyl)-cyclopropane-1R-carboxylate, 3-phenoxy-benzyl 2,2-dimethyl-3S-(1',2',2',2'-tetrabromoethyl)cyclopropane-1R-carboxylate,
   (S) 1-oxo-2-allyl-3-methyl-cyclopent-2-en-4-yl 2,2-dimethyl-3R-(1',2'-dibromo-2',2'-dichloroethyl)-cyclopropane-1R-carboxylate,
   (R,S) α-cyano-3-phenoxy-benzyl 2,2-dimethyl-3S-(1',2'-dichloro-2',2'-dibromoethyl)-cyclopropane-1R-carboxylate, (S) 1-oxo-2-allyl-3-methyl-cyclopent-2-en-4-yl 2,2-dimethyl-3S-(1',2'-dichloro-2',2'-dibromoethyl)-cyclopropane-1R-carboxylate, (R,S) α-cyano-3-phenoxy-benzyl 2,2-dimethyl-3R-(1',2'-dichloro-2',2'-dibromoethyl)-cyclopropane-1R-carboxylate, (S) 1-oxo-2-allyl-3-methyl-cyclopent-2-en-4-yl 2,2-dimethyl-3R-(1',2'-dibromo-2',2'-difluoroethyl)-cyclopropane-1R-carboxylate and (R,S) α-cyano-3-phenoxy-benzyl 2,2-dimethyl-3S-(1',2'-dibromo-2',2'-dichloroethyl)-cyclopropane-1R-carboxylate.

11. A compound of claim 1 in the form of its diastereoisomers with respect to the asymetric carbon atom in the 1'-position or mixtures thereof selected from the group consisting of (R,S) α-cyano-3-phenoxy-benzyl 2,2-dimethyl-3S-(1',2',2',2'-tetrabromoethyl)-cyclopropane-1R-carboxylate, 3-phenoxy-benzyl 2,2-dimethyl-3R-(1',2',2',2'-tetrabromoethyl)-cyclopropane-1R-carboxylate, 3-phenoxy-benzyl 2,2-dimethyl-3S-(1',2',2',2'-tetrachloroethyl)-cyclopropane-1R-carboxylate, (R,S) α-cyano-3-phenoxy-benzyl 2,2-dimethyl-3S-(1',2',2',2'-tetrachloroethyl)-cyclopropane-1R-carboxylate, 3-phenoxy-benzyl 2,2-dimethyl-3S(1',2',2',2'-tetrachloroethyl)-cyclopropane-1R-carboxylate, (R,S) allethrolone 2,2-dimethyl-3S-(1',2',2',2'-tetrachloroethyl)-cyclopropane-1R-carboxylate, (R,S) α-cyano-3-phenoxy-benzyl 2,2-dimethyl-3R-(1',2',2',2'-tetrachloroethyl)-cyclopropane-1R-carboxylate, 3-phenoxy-benzyl 2,2-dimethyl-3R-(1',2',2',2'-tetrachloroethyl)-cyclopropane-1R-carboxylate, (S) allethrolone 2,2-dimethyl-3R-(1',2',2',2'-tetrachloroethyl)-cyclopropane-1R-carboxylate, (S) allethrolone 2,2-dimethyl-3S-(1',2'-dibromo-2',2'-dichloro-ethyl)-cyclopropane-1R-carboxylate, 3-phenoxy-benzyl 2,2-dimethyl-3S-(1',2'-dibromo-2',2'-dichloroethyl)-cyclopropane-1R-carboxylate, (R,S) α-cyano-3-phenoxy-benzyl dl cis trans 2,2-dimethyl-3-(1',2'-dibromo-2',2'-dichloroethyl)-cyclopropane-1-carboxylate, 3-phenoxy-benzyl 2,2-dimethyl-3R-(1',2'-dibromo-2',2'-dichloroethyl)-cyclopropane-1R-carboxylate, (S) allethrolone 2,2-dimethyl-3R-(2',2'-dibromo-1',2'-dichloroethyl)-cyclopropane-1R-carboxylate, 3-phenoxy-benzyl 2,2-dimethyl-3R-(1',2'-dichloro-2',2'-dibromoethyl)-cyclopropane-1R-carboxylate, 3-phenoxy-benzyl 2,2-dimethyl-3S-(1',2'-dichloro-2',2'-dibromoethyl)-cyclopropane-1R-carboxylate, (S) allethrolone 2,2-dimethyl-3S-(1',2'-dibromo-2',2'-difluoroethyl)-cyclopropane-1R-carboxylate, (R,S) α-cyano-3-phenoxy-benzyl 2,2-dimethyl-3S-(1',2'-dibromo-2',2'-difluoroethyl)-cyclopropane-1R-carboxylate, 3-phenoxy-benzyl 2,2-dimethyl-3R-(1',2'-dibromo-2',2'-difluoroethyl)-cyclopropane-1R-carboxylate, (R,S) α-cyano-3-phenoxy-benzyl 2,2-dimethyl-3R-(1',2'-dibromo-2',2'-difluoroethyl)-cyclopropane-1R-carboxylate and 3-phenoxy-benzyl 2,2-dimethyl-3S-(1',2'-dibromo-2'-chloro-2'-fluoroethyl)-cyclopropane-1R-carboxylate.

12. A compound of claim 1 in the form of its diastereoisomers with respect to the asymetric carbon atom in the 1'-position or mixtures thereof selected from the group consisting of (S) α-cyano-3-phenoxy-benzyl (1R,trans) 2,2-dimethyl-3-(2',2'-dichloro-1',2'-dibromoethyl)-cyclopropane-1-carboxylate, (S) α-cyano-3-phenoxy-benzyl (1R, cis) 2,2-dimethyl-3-(2',2'-dibromo-1',2'-dichloroethyl)-cyclopropane-1-carboxylate, (S) α-cyano-3-phenoxy-benzyl (1R, cis) 2,2-dimethyl-3-(1',2',2',2'-tetrachloroethyl)-cyclopropane-1-carboxylate and (R) α-cyano-3-phenoxy-benzyl (1R, trans) 2,2-dimethyl-3-(2',2'-dichloro-1',2'-dibromoethyl)-cyclopropane-1-carboxylate.

13. A compound of claim 1 in the form of its diastereoisomers with respect to the asymetric carbon atom in the 1'-position or mixtures thereof which is the (S) α-cyano-3-phenoxy-benzyl (1R, trans) 2,2-dimethyl-3-(2',2'-dichloro-1',2'-dibromoethyl)-cyclopropane-1-carboxylate.

14. A compound of claim 1 in the form of a mixture of cis and trans structures in any proportion.

15. A compound of claim 14 wherein the proportions by weight are 20/80, 50/50 or 80/20.

16. A compound of claim 1 which is (S) α-cyano-3-phenoxy-benzyl 2,2-dimethyl-3S-(1',2',2',2'-tetrabromoethyl)-cyclopropane-1R-carboxylate in the form of its diastereoisomers with respect to the asymetric carbon atom in the 1'-position or mixtures thereof.

* * * * *

UNITED STATES PATENT AND TRADEMARK OFFICE
CERTIFICATE OF CORRECTION

PATENT NO. : 4,279,835
DATED : July 21, 1981
INVENTOR(S) : JACQUES MARTEL ET AL.

Page 1 of 3

It is certified that error appears in the above—identified patent and that said Letters Patent is hereby corrected as shown below:

Preamble page, [57] Abstract, second column, after the last structural formula, please insert -- 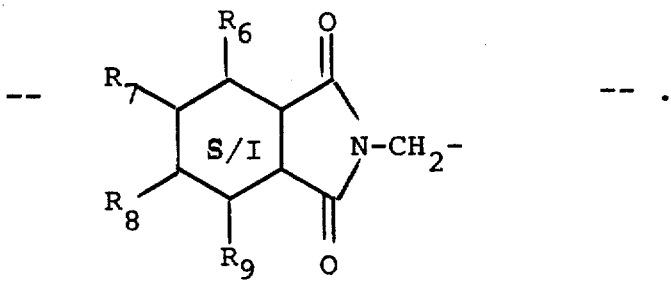 -- .

Column 2, line 17: Delete "$_L$" after "$R_3$".

line 28: "benzoyl" should read -- benzyl --.

Column 3, line 25: "2,2dimethyl" should read -- 2,2-dimethyl --.

Column 10, line 35: "hydo" should read -- hydro --.

Column 11, line 12: "C=N" should read -- C≡N -- line 66: "dimethyl-B 3R" should read -- dimethyl-3R --.

Column 17, line 61: "1-R" should read -- 1R --.

Column 18, line 35: "STEP C: (R,5)" should read -- STEP C: (R,S) --.

Column 20, line 26: "$C_gH_{10}Cl_4O_2$" should read -- $C_8H_{10}Cl_4O_2$ --.

UNITED STATES PATENT AND TRADEMARK OFFICE
CERTIFICATE OF CORRECTION

PATENT NO. : 4,279,835

DATED : July 21, 1981

INVENTOR(S) : Jacques Martel et al.

Page 2 of 3

It is certified that error appears in the above—identified patent and that said Letters Patent is hereby corrected as shown below:

Column 21, line 2: "4,35" should read -- 4,36 --.

Column 22, line 40: "or" should read -- on --.

Column 30, line 59: "1783 cm$^-$" should read -- 1783 cm$^{-1}$ --.

Column 36, line 15: "or" should read -- of --.

Column 39, line 11: "tetrachloric" should read -- tetrachloride --.

Column 46, line 45: "c±0.5% should read -- c = 0.5% --.

Column 49, line 23: "1',2°,2',2'-" should read -- 1',2',2',2'- --.

Column 50, line 17: "1 µ" should read -- 1 µl --.

UNITED STATES PATENT AND TRADEMARK OFFICE
CERTIFICATE OF CORRECTION

PATENT NO. : 4,279,835
DATED : July 21, 1981
INVENTOR(S) : JACQUES MARTEL ET AL.

Page 3 of 3

It is certified that error appears in the above—identified patent and that said Letters Patent is hereby corrected as shown below:

Column 56, line 19 (Claim 1): "-C/CH," should read -- -C≡CH, --.

Column 56, line 44; Column 58, line 32: "diastere-" should read -- diastereo- --.

Column 56, line 45; Column 58, line 33: "oisomers" should read -- isomers --.

Signed and Sealed this

Fifth Day of January 1982

[SEAL]

Attest:

Attesting Officer

GERALD J. MOSSINGHOFF
Commissioner of Patents and Trademarks